US008735135B2

(12) United States Patent
Fujii et al.

(10) Patent No.: US 8,735,135 B2
(45) Date of Patent: May 27, 2014

(54) TRANSFORMED STRAINS ORIGINATED FROM MULTIDRUG EFFLUX PROTEIN DEFECTIVE STRAINS AND A METHOD FOR MICROBIAL CONVERSION USING THEM

(75) Inventors: Tadashi Fujii, Tokyo (JP); Atsushi Ochiai, Tokyo (JP); Masashi Ito, Tokyo (JP); Hiroki Kabumoto, Tokyo (JP); Yoshikazu Fujii, Tokyo (JP); Kazuhiro Machida, Tokyo (JP)

(73) Assignee: Microbiopharm Japan Co., Ltd, Tokyo (JP)

( * ) Notice: Subject to any disclaimer, the term of this patent is extended or adjusted under 35 U.S.C. 154(b) by 547 days.

(21) Appl. No.: 12/449,868

(22) PCT Filed: Feb. 28, 2008

(86) PCT No.: PCT/JP2008/053565
§ 371 (c)(1),
(2), (4) Date: Jan. 11, 2010

(87) PCT Pub. No.: WO2008/105513
PCT Pub. Date: Sep. 4, 2008

(65) Prior Publication Data
US 2012/0040441 A1 Feb. 16, 2012

(30) Foreign Application Priority Data
Mar. 1, 2007 (JP) .................................. 2007-050935

(51) Int. Cl.
*C12N 1/21* (2006.01)
*C12P 1/04* (2006.01)
(52) U.S. Cl.
USPC ...................................... 435/252.33; 435/170
(58) Field of Classification Search
None
See application file for complete search history.

(56) References Cited

U.S. PATENT DOCUMENTS

2003/0215915 A1* 11/2003 Wolf et al. ................... 435/69.1

FOREIGN PATENT DOCUMENTS

| JP | 11-221080 | 8/1999 |
| JP | 2005-504530 | 2/2005 |
| WO | WO 03/018817 | 3/2003 |
| WO | WO 2007/138894 | 12/2007 |

OTHER PUBLICATIONS

Srikumar et al (Antimicrob. Agents Chemother., 1998, vol. 42, No. 1, p. 65-71).*
Potrykus et al. (Arch. Microbiol., 180:362-366, 2003).*
Srikumar, R (1998).Expression of *Pseudomonas aeruginosa* multidrug efflux pumps MexA-MexB-OprM and MexC-MexD-OprJ in a multidrug-sensitive *Escherichia coli* strain. *Antimicrobial Agents and Chemotherapy*, 42(1), 65-71.
Nakamura, K. (2001). Functional expression of *Candida albicans* drug efflux pump Cdrlp in a *Saccharomyces cerevisiae* strain deficient in membrane transporters. *Antimicrobial Agents and Chemotherapy*, 45(12), 3366-3374.
Niimi, M. (2004). An efficient system for functional hyper-expression of multidrug efflux pumps in *Saccharomyces cerevisiae*. *Jpn. J. Med. Mycol.*, 45(2), 63-69.
Arisawa, A (2003). Construction of biotransformation system by *Escherichia coli* strains coexpressing genes for actinomycete cytochrome P450 monoxygenases and redox partner proteins. *The society for Actinomycetes Japan Taikai Koen Yoshishu*, 18, 36.
Watanabe, I. (1995). Cloning, characterization and expression of the gene encoding cytochrome P-450 sca-2 from *Streptomyces carbophilus* involved in production of pravastatin, a specific HMG-CoA reductase inhibitor. *Gene*, 163, 81-85.
Sawada, N. (2004). Conversion of vitamin D3 to Alpha, 25-dihydroxyvitamin D3 by *Streptomyces griseolus* cytochrome P450SU-1. *Biochem. Biophys. Res. Commun.*, 320, 156-164.
Uchida, E. (2004). Purification and characterization of mouse CYP27B1 overproduced by an *Escherichia coli* system coexpressing molecular chaperoning GroEL/ES. *Biochem. Biophys. Res. Commun.*, 323, 505-511.
Wada, A. (1991). Expression of functional bovine cholesterol side chain cleavage cytochrome P450 (P450scc) in *Escherichia coli*. *Arch. Biochem. Biophys.*, 290(2), 376-380.
Sugano, S. (1995). Cytochrome P-450scc catalyzed production of progesterone from cholestenone. *Biochem. Mol, Biol. Int.*, 35(1), 31-36.
Fujii, T. (2002). Biotransformation of L-lysine to L-pipecolic acid catalyzed by L-lysine 6-aminotransferase and pyrroline-5-carboxylate reductase. *Bioci. Biotechnol. Biochem.*, 66(3), 622-627.
Fujii, T. (2002). Increase in the rate of L-pipecolic acid production using lat-expressing *Escherichia coli* by lysP and yeiE amplification. *Biosci. Biotechnol. Biochem.*, 66(9), 1981-1984.
Elkins, C. A. and Mullins, L.B. (2006). Mammalian steroid hormones are substrates for the major RND- and MFS-type tripartite multidrug efflux pumps of *Escherichia coli*. *J. Bacterial.*, 188(3), 1191-1195.
Takeda, K. (2006). Isolation and identification of 2alpha, 25-dihydroxyvitamin D3, a new metabolite from *Pseudo nocardia autotrophic* 100U-19 cells incubated with vitamin D3. *Steroids*, 71, 736-744.
Fujii, T. (2006). Production of alpha, omega-alkanediols using *Escherichia coli* expressing a cytochrome P450 from *Acinetobacter* sp. OC4. *Biosci. Biotechnol. Biochem.*, 70(6), 1379-1385.
Brown, et al. "Two host-induced *Ralstonia solanacearum* genes, acrA and dinF, encode multidrug efflux pumps and contribute to bacterial wilt virulence." Applied and Environmental Microbiology, vol. 73, No. 9, Mar. 2, 2007, pp. 2777-2786.

(Continued)

*Primary Examiner* — Brian J Gangle
(74) *Attorney, Agent, or Firm* — Jacobson Holman PLLC

(57) ABSTRACT

Disclosed is a means for improving the poor conversion efficiency in a conventional bioconversion system using a transformant which is given by introducing a gene originated from xerogenic organisms. A transformant is prepared by using a host which is defective in a gene encoding a multidrug efflux protein and introducing a gene originated from xerogenic organisms. Use of the transformant results in much effective microbial conversion of a hydrophobic or amphipathic substrate compound into a desired compound. In case, an *Escherichia coli* is used as the host, the gene encoding a multidrug efflux protein to be defective may be tolC, acrA, acrB and the like.

4 Claims, No Drawings

(56) References Cited

OTHER PUBLICATIONS

De Cristobal et al. "Multidrug resistance pump AcrAB-TolIC is required for high-level, Tet(A)-mediated tetracycline resistance in *Escherichia coli*." Journal of Antimicrobial Chemotherapy, vol. 58, No. 1, Jul. 2006, pp. 31-36.

Fujii et al. "Efficient biotransformations using *Esherichia coli* with tolC acrAB mutations expressing cytochrome P450 genes." Bioscience Biotechnology and Biochemistry, vol. 73, No. 4, Apr. 2009, pp. 805-810.

Bernhardt et al. "Cytochromes P450 as versatile biocatalysts" Journal of Biotechnology, 124 (2006) 128-145.

Chatterjee et al. "A general genetic approach in *Escherichia coli* for determining the mechanism(s) of action . . . " Proc. Natl. Acad. Sci., v. 92, pp. 8950-8954, Sep. 1995.

Doukyu et al. "Indigo production by *Escherichia coli* carrying the phenol hydroxylase gene from *Acinetobacter* . . . " Appl Microbial Biotechnol (2003) 60:720-725.

Tsukagoshi et al. "Entry into and release of solvents by *Escherichia coli* in an organic-aqueous . . . " Journal of Bacteriology, v. 182, n. 17, Sep. 2000, pp. 4803-4810.

Potrykus J, and Wegrzyn G. Arch. Microbiol, 180/5, pp. 362-366, Nov. 2003.

\* cited by examiner

TRANSFORMED STRAINS ORIGINATED FROM MULTIDRUG EFFLUX PROTEIN DEFECTIVE STRAINS AND A METHOD FOR MICROBIAL CONVERSION USING THEM

CROSS-REFERENCE TO RELATED APPLICATIONS

This application is a 371 of PCT/JP08/053565 filed Feb. 28, 2008, which claims benefit of priority to Japanese Patent Application No. 2007-50935 filed on Mar. 1, 2007, which is expressly incorporated herein by reference in its entirety.

TECHNICAL FIELD

The present invention relates to transformed strains which are given by introducing a gene originated from xenogeneic organisms into a host which is defective in multidrug efflux protein, and to a method for microbial conversion of a substrate compound using them.

BACKGROUND ART

In general, the means of producing compounds include chemical synthesis and enzymatic synthesis. In order to produce the compounds which can be materials for a variety of pharmaceutical products, it is essential to efficiently carry out regiospecific and stereospecific modifications of starting compounds. It is known that the enzymatic synthesis is superior in terms of these reactions.

In order to utilize an enzyme as a practical catalyst at an industrial level, however, the fundamental margin of the enzyme has to be considered. It comprises a short life span of the enzyme and the necessity of a coenzyme for catalytic events. Much attention has been paid so far to the way to elongate the life span of the enzyme and to retain the enzyme activity in the design for manufacturing processes with the enzyme. In addition, most enzymes used for the enzymatic synthesis require coenzymes in the catalytic events, and, for example, enzyme reactions for oxidation-reduction require a pyridine nucleotide such as NADH. These coenzymes are expensive in general, and therefore the addition of coenzyme has become an economically major issue when performing enzyme reactions at an industrial level.

As a solution to overcome of the margin of these enzyme reactions, a strategy using cells of a microorganism, particularly of *E. coli*, as a field for the enzyme reaction has been developed. That is, by means of transforming *E. coli* with an enzymatic gene, the target enzyme can be abundantly expressed within the cell. This means that the enzyme is continuously produced in the cell, and the enzyme activity can be retained as long as the cell is alive. Furthermore, a variety of intracellular reactions of metabolism enable the coenzymes required for the enzyme reactions to be regenerated.

An attempt has been made to produce the chemical substances which can be varieties of pharmaceutical materials by means of "microbial conversion" which comprises cultivating such a transformant of *E. coli* in a culture medium and bringing the culture contact with a substrate compound to obtain the modified compound. In particular, the oxidation reaction by microbial conversion of a hydrophobic or amphipathic compound using *E. coli* which has been transformed with a cytochrome P-450 gene has importance in pharmaceutical manufacturing.

A cytochrome P-450 enzyme which is encoded with a cytochrome P-450 gene (hereinafter also simply referred to as a P-450 enzyme) is the generic term for a group of the protoheme containing protein which is bound to carbon monoxide in its reduced form to give the soret band at around 450 nm. The P-450 enzyme is bound to tissues of most animals and plants, microsome of molds and yeasts and mitochondrial inner membrane of a part of animal tissues, and it exists in some kinds of bacteria and molds in its soluble form.

The P-450 enzymes have a variety of substrate specificity. There are enzymes exhibiting extraordinary wide substrate specificity which can utilize a large variety of organic compounds as the substrate, whereas some enzymes are found to have a rather strict substrate specificity which reacts only with comparatively limited kinds of organic compounds. Also some show excellent selectivity in stereo-specificity or regio-specificity to the reaction site. In addition, it is known that the P-450 enzymes are involved in, as specific functions, a wide variety of reactions such as xenobiotic hydroxylation, epoxidation, dealkylation and denitrogenation within the cells exhibiting the P-450 enzymes by catalyzing the monooxygenation.

In particular, a part of the P-450 enzymes originated from microorganisms have practically been utilized for industrial production of useful compounds. One of the typical examples is the P-450 enzyme of *Streptomyces carbophilus*, which hydroxylates the 6α-position of compactin, a substrate, to produce pravastatin as a product which is a therapeutic agent for hyperlipidemia (see Non Patent Literature 1). Furthermore, the method of producing active vitamin $D_3$ by hydroxylating the 1α-position and the 25-position of vitamin $D_3$ utilizing the P-450 enzyme of the ATCC33795 strain of *Pseudonocardia autotrophica* has been put to practical use. These P-450 enzymes originated from the microorganism can catalyze the monooxygenation only by conjugating with the electron transport system (ferredoxin and ferredoxin reductase) which donates electrons to the enzymes.

Such microbial conversion of compounds using cytochrome P-450 enzyme originated from microorganisms has been performed by using a culture solution or bacterial body of the microorganism which was expressing the enzyme. Another culture solution has also been used which is given by introducing a gene encoding the P-450 enzyme originated from microorganisms into *Streptomyces lividans* suitable as a host, and caused to express its enzyme activity. However, the microbial conversion of a substrate compound by an actinomycete having such a gene requires considerable time for culturing and converting the substrate compound into the objective product because of the unique nature of actinomycetes. In addition, depending upon the enzyme, investigation of the expression inducing conditions is required for effectively increasing the expression level of the enzyme. Furthermore, some actinomycetes used for the conversion have a reaction system which metabolizes or degrades the substrate compound or the objective product, and this contributes to generation of byproducts and decrease in the substrate compound and the objective product to lower the productivity of the objective product.

For these reasons, it has been desired to establish a system which can functionally express the cytochrome P-450 gene originated from microorganisms and which uses as the host an *E. coli* requiring relatively short period of time for culture and also being considered to have less reaction systems to metabolize or degrade the substance compound and the objective product. As such a system, a system has been proposed that co-expresses the camAB gene encoding the electron transport system of P450cam and causes to functionally express the cytochrome P-450 gene of a wide variety of actinomycetes (see Patent Document 1). However, the activity of microbial conversion by this system was quite low and inadequate to be utilized in industrial production. Thus, in order to actually perform the industrial production by microbial conversion using *E. coli* which expresses the gene encoding the cytochome P-450 enzyme originated from microorganisms, further improvement of the activity has been required.

As the technique for it, the method of actively introducing the substance into the cell has been examined. For example, the *E. coli* caused to express the lat gene encoding L-lysine 6-aminotransferase originated from the IFO3084 strain of *Flavobacterium lutescens* is capable of converting L-lysine into L-pipecolic acid (see Non Patent Literature 2), and it is known that, in the microbial conversion using the transformant, the microbial conversion activity is improved by amplifying the lysP gene which encodes the L-lysine specific permease in order to actively introduce the substrate L-lysine into the cell (see Non Patent Literature 3).

Thus, in microbial conversion, it has been suggested that the membrane transport of substrate molecules into the cells is the important affair, but no mechanism exists in *E. coli* which actively perform the membrane transport into the cells the hydrophobic or amphipathic compounds which are frequently used as substrate compounds in microbial conversion for drug manufacturing. In addition, it has been reported that the intracellular abundance of the given compound (mammalian steroidal hormone) increases in the strain of *E. coli* subjected to disruption of drug efflux protein (see Non Patent Literature 4). This suggests the increase of the intracellular abundance on the ground that the compound passively penetrating into the cell becomes difficult to be eliminated from the body.

On the other hand, a patent application has been published of which the gist is that the *E. coli* subjected to transformation with at least one gene of acrA, acrB or tolC gene which encodes the drug efflux protein is provided with resistance to organic solvents, and the microbial conversion in the bilayer system using this *E. coli* can be performed with high efficiency (Patent Literature 2). These matters show it difficult to presume the effect of the disruption of multidrug resistant protein of the host microorganism on the microbial conversion.

[Patent Literature 1] Brochure of International Publication No. 2003/087381, its family in English US 2006234337 A1

[Patent Literature 2] Japan Patent Application Laid-open disclosure Kokai number Heisei 11-221080 (221080/1999A1)

[Non Patent Literature]

[Non Patent Literature 1] Cloning, characterization and expression of the gene encoding cytochrome P-450sca-2 from *Streptomyces carbophilus* involved in production of pravastatin, a specific HMG-CoA reductase inhibitor. Gene. 1995 September 22;163(1):81-85.

[Non Patent Literature 2] Microbial conversion of L-lysine to L-pipecolic acid catalyzed by L-lysine 6-aminotransferase and pyrroline-5-carboxylate reductase. Biosci Biotechnol Biochem. 2002 March; 66(3):622-627.

[Non Patent Literature 3] Increase in the rate of L-pipecolic acid production using lat-expressing *Escherichia coli* by lysP and yeiE amplification. Biosci Biotechnol Biochem. 2002 September; 66(9):1981-1984.

[Non Patent Literature 4] Mammalian steroid hormones are substrates for the major RND- and MFS-type tripartite multidrug efflux pumps of *Escherichia coli*. J Bacteriol. 2006 February; 188(3):1191-1195.

[Non Patent Literature 5] Entry into and release of solvents by *Escherichia coli* in an organic-aqueous two-liquid-phase system and substrate specificity of the AcrAB-TolC solvent-extruding pump. J Bacteriol. 2000 September; 182 (17):4803-10.

[Non Patent Literature 6] Production of alpha, omega-alkanediols using *Escherichia coli* expressing a cytochrome P450 from *Acinetobacter* sp. OC4. Biosci Biotechnol Biochem. 2006 June;70(6):1379-1385.

All the descriptions of the abovementioned Patent Literatures 1 and 2, and Non Patent Literatures 1 to 6 are expressly incorporated herein by reference in their entirety.

The object of the present invention is to provide a means for improving the low conversion efficiency shown in the present microbial conversion which uses the transformant inserted with a gene originated from xenogeneic organisms.

DISCLOSURE OF THE INVENTION

In order to achieve the object above, the present inventors prepared a transformant which are given by inserting a gene originated from a xenogeneic organism into a host which is defective in any one of some genes encoding multidrug efflux protein. In addition, they found that this transformant converts the hydrophobic or amphipathic substrate compound into its objective compound in high efficiency to attain the present invention.

Thus, the present invention relates to the following [1] to [9].

[1] A transformant which is given by introducing a gene originated from a xenogeneic organism into a host microorganism which is defective in any gene of the genes encoding multidrug efflux protein.

[2] The transformant according to [1] wherein the host microorganism which is defective in a gene encoding multidrug efflux protein is *E. coli*.

[3] The transformant according to [1] or [2] wherein the gene encoding multidrug efflux protein is any gene selected from the group consisting of tolC, acrA and acrB.

[4] The transformant according to any one of [1 ] to [3] wherein the gene originated from a xenogeneic organism is a gene encoding any enzyme selected from the group consisting of oxidoreductase, transferase, hydrolase, lyase, isomerase and synthetase.

[5] The transformant according to any one of [1] to [3] wherein the gene originated from a xenogeneic organism is a gene encoding cytochrome P-450 enzyme or aminotransferase.

[6] The transformant according to any one of [1] to [3] wherein the gene originated from a xenogeneic organism is a gene encoding cytochrome P-450 enzyme.

[7] A method of microbial conversion which uses the transformant according to any one of [4] to [6].

[8] A method of microbial conversion which uses the transformant according to any one of [4] to [6], characterized by performing monooxygenation to a substrate compound.

[9] The method according to [8] wherein the substrate compound is selected from the group consisting of vitamin $D_3$, 4-cholesten-3-one and compactin.

Hereinafter the definition of the terms, symbols and so on described herein will be explained, and the present invention will be illustrated in detail.

The term "multidrug efflux protein" used herein includes all the protein existing in Gram-negative bacteria and mainly constituting the drug resistance mechanism which eliminates hydrophobic and amphipathic compounds from the inside of bacterial bodies to the outside. It comprises TolC, AcrA, AcrB, EmrA, EmrB and so on from *E. coli* and OprM, MexA, MexB and so on from *Pseudomonas aeruginosa* fall into this category without limitation.

The term "a gene originated from a xenogeneic organism" used herein includes all the genes which can be isolated or amplified from a living organism other than the microorganism to be used as the host. It comprises the genes isolated or amplified from chromosomal DNA and plasmid DNA of a living organism, those amplified from mRNA, and so on without limitation.

The term "a transformant" used herein means a microorganism which is given by inserting into a specific microorganism a gene originated from another living organism in an expressible form by means of genetic recombination technologies, and the technique for gene transfer used for them includes not only the gene recombination using a vector such as plasmid but also homologous recombination and so on.

The term "microbial conversion" used herein means a method of culturing a transformant in a medium, bringing the culture into contact with a substrate compound, modifying the compound to convert into the objective compound, and obtaining it.

The term "a substrate compound" in the present invention means a hydrophobic or amphipathic compound which can be modified by various kinds of microbial conversion reactions. For example, when the gene originated from a xenogeneic organism is a P450 gene, it includes alkane compounds such as hexane, heptane, octane and nonane, aromatic compounds such as toluene, phenol and cumene, steroids such as cholesterol, testosterone, 4-cholesten-3-one, dehydroepiandrosterone, vitamin $D_2$ and vitamin $D_3$, linear peptides such as leucyl-leucine, leucylvaline, polyleucine and polyvaline, diketopiperazines which are given by cyclocondensation of a dipeptide such as prolylphenylalanine and leucylalanine, cyclic peptides having physiological activity such as cyclosporine and echinomycin, monoterpenes such as pinene, camphene, limonene and geraniol, sesquiterpenes such as ambrosane, caryophyllane and drimane, diterpenes such as abietic acids and gibberellic acids, triterpenes such as dammarane, hopane and lanostane, statins such as compactin, macrolides such as tylosin, FK-506 and erythromycin, and also various kinds of drugs, or their precursors, metabolites, derivatives, and so on.

The term "a gene analogue" used herein means a polynucleotide which has substantially the same functions as the original gene, and
(1) which hybridizes with the original gene under the stringent conditions,
(2) which has a nucleotide sequence having 70% or more homology with that of the original gene,
(3) which has a nucleotide sequence complementary to that of the original gene, or
(4) which does not hybridize with the original gene under the stringent conditions because of degeneracy of genetic codes, but which has a nucleotide sequence encoding the same sequence as the amino acid sequence encoded by the polynucleotide defined in any one of (1) to (3).

In addition, the term "a polynucleotide which hybridizes under the stringent conditions" means, for example, a polynucleotide obtained by using colony hybridization technique, plaque hybridization technique or southern hybridization method and so on in which the original gene is used as the probe, and in particular, it includes a polynucleotide which can be identified by performing hybridization with the filter which is fixed with a polynucleotide originated from a colony or plaque in the presence of 0.7 to 1.0M sodium chloride at 65° C., and then cleaning the filter with the SSC solution in 0.1 to 2 times the concentration (the composition of the SSC solution in 1 time the concentration is composed of 150 mM sodium chloride and 15 mM sodium citrate) under the condition of 65° C.

According to the present invention, a transformant which is given by introducing a gene originated from a xenogeneic organism into a host which is a microorganism defective in the gene encoding multidrug efflux protein can be prepared, and by using the transformant, various kinds of substrate compounds can be efficiently converted into the objective compounds.

BEST MODE FOR CARRYING OUT THE INVENTION

Hereinafter, embodiments of the present invention will be described in detail.

Host Defective in the Gene Encoding Multidrug Efflux Protein

In the present invention, first, a host defective in the functions of multidrug efflux protein which are those the microorganism to be used as the host originally owns is prepared. In this host, a part or all of the gene encoding multidrug efflux protein is missing, or the gene is segmented by being inserted into its inside with another DNA, or the gene has at least one mutation, so that a part or all of the functions of the multidrug efflux protein encoded by the gene is lost (or sometimes referred to as "being disrupted"). Such a microorganism with disrupted genetic functions is not limited, but it can be obtained by the use of the known P1 transduction technique or homologous DNA recombination technique. The host microorganism is not particularly limited as long as it can be cultured and used for amplification of the inserted gene with vector such as plasmid or phage DNA, and it includes, for example, microorganisms belonging to *E. coli, Flavobacterium, Pseudomonas,* and *Corynebacterium,* and the preferred example includes *E. coli.*

The gene encoding multidrug efflux protein is not limited, but includes, for example, as ones originated from *E. coli,* tolC which is the gene encoding TolC that is a multidrug efflux protein originated from the *E. coli* K-12 strain and represented by the continuous nucleotide sequence starting from Nucleotide No. 1 to Nucleotide No. 1488 in SEQ ID No. 22, acrA which is the gene encoding AcrA that is a multidrug efflux protein originated from the *E. coli* K-12 strain and represented by the continuous nucleotide sequence starting from Nucleotide No. 329 to Nucleotide No. 1522 in SEQ ID No. 23, acrB which is a gene encoding AcrB that is a multidrug efflux protein originated from the *E. coli* K-12 strain and represented by the continuous nucleotide sequence starting from Nucleotide No. 1545 to Nucleotide No. 4694 in SEQ ID No.23, or their analogues.

The host microorganisms thus obtained is defective in a part or all of the functions of multidrug efflux protein, so that the substrate compound is considered to easily stay within the microorganism in microbial conversion, and as the result, the conversion efficiency and also the production efficiency of the objective product get higher. ps Preparation of the transformant The gene originated from a xenogeneic microorganism or its analogue (hereinafter sometimes simply referred to as "xenogeneic genes") is then incorporated into the resulting host to prepare a transformant suitable for microbial conversion. The method for incorporating the xenogeneic genes into the host is not particularly limited, and for example, the xenogeneic genes can be inserted into an appropriate vector to be incorporated into the host by the protoplast method, or electroporation method. The kind of the vector which can be used is not particularly limited, and for example, autonomously-replicating vectors (e.g., plasmid etc.) may be used, or vectors which have been incorporated into genome of the host cell when introducing into the host and is replicated together with the incorporated chromosome may also be used, but expression vectors are preferred. In expression vectors, the xenogeneic genes and so on are functionally connected with elements which are essential for transcription (e.g., promoter etc.). Promoter is a DNA sequence which exhibits transcription activity in the host cell, and it can be selected appropriately depending upon the kinds of the host.

Gene originated from xenogeneic organism

The xenogeneic genes and so on incorporated into the host are not particularly limited as long as they are involved in the reaction to convert the substrate compound into the objective compound, but the genes encoding kinds of enzymes which directly catalyze the conversion are preferred, and for example, they include oxidoreductase, transferase, hydrolase, lyase, isomerase and synthetase. The oxidoreductase is not particularly limited as long as it is an enzyme to catalyze redox reaction, and includes cytochrome P-450 enzyme, aldehyde reductase and so on. The most preferred includes cytochrome P-450 enzyme, especially that categorized into the CYP105 family and the CYP107 family. The transferase is not particularly limited as long as it is an enzyme to transfer an atom group (such as a functional group) from a molecule to another one, and includes aminotransferase (catalyzing the reaction to give the a-amino group of the substrate compound to the 2-oxoglutaric acid and to make the substrate compound itself to be 2-oxo acid), glycosyltransferase and so on.

The hydrolase is not particularly limited as long as it is an enzyme to catalyze hydrolysis, and it includes lipase, amylase and so on. The lyase is not particularly limited as long as it is an enzyme to catalyze dissociation of bonds between atom groups, and it includes carbonic hydratase and so on. The isomerase is not particularly limited as long as it is an enzyme to catalyze a reaction to substrate-specifically isomerize an isomer, and it includes glucose isomerase and so on. The synthetase is not particularly limited as long as it is an enzyme to combine two molecules by utilizing hydrolysis energy of ATP, and it includes DNA ligase and so on.

Cultivation of the Transformant

The transformant thus prepared is cultured in an appropriate nutritive medium under the conditions to enable expression of the inserted gene, if needed, by addition of an inducer and so on. Such a nutritive medium consists of appropriate carbon sources, nitrogen sources, inorganic salts and natural organic nutrients and so on, and as the carbon sources, one or more kinds of glucose, fructose, glycerol, sorbitol, organic acids and so on can be used, and as the nitrogen sources, one or more kinds of compounds such as ammonia, urea, ammonium sulfate, ammonium nitrate and ammonium acetate can be used. As the inorganic salt, salts such as potassium phosphate, dipotassium phosphate, magnesium sulfate, manganese sulfate, and ferrous sulfate can be used. Moreover, as the natural organic nutrients which have a growth-promoting effect on the bacterium to be used, peptone, meat extract, yeast extract, corn steep liquor, casamino acid and so on can be used, and a small amount of vitamins and nucleic acids can be contained.

Microbial Conversion Using the Transformant

Then the bacterial body expressing these genes is brought into contact with the substrate compound to perform the conversion reaction. The temperature in the conversion reaction can appropriately be determined in view of the optimum temperature of the transformant. The reaction time can also be determined appropriately in view of the conversion into the objective compound (the progress degree of the reaction) and so on. When the host is *E. coli*, for example, the reaction is preferably performed at 20 to 37° C. for 1-5 days. Moreover, the reaction mode may be batch type or continuous type, or the reaction can be performed in any style.

For the isolation and purification of the generated objective product, the isolation and purification methods generally used for isolating the microbial metabolite from its culture solution can be utilized. For example, they include any known methods such as organic solvent extraction using methanol, ethanol, acetone, butanol, ethyl acetate, butyl acetate, chloroform, toluene and so on, adsorption-desorption treatment using hydrophobic adsorption resin such as DIAION HP-20, gel filtration chromatography using SEPHADEX LH-20 and so on, adsorption chromatography with active carbon, silica gel and so on, or adsorption-desorption treatment by thin layer chromatography, or high-performance liquid chromatography using a reverse-phase column, and others. However, the methods are not particularly limited to those mentioned here. By means of using these methods singularly or in combination in any order or repeatedly, the objective compound can be isolated and purified.

EXAMPLES

Hereinafter, the present invention will be explained in more detail with specific examples, but it is not intended to limit the present invention to these examples. The percentage (%) in the following examples indicates percent by weight in the explanation of the culture media, and percent by volume in that of the mobile phase of HPLC.

Example 1

Construction of the *E. coli* tolC Disrupted Strain

From the *E. coli* CAG12184 (tolC::Tn10) strain obtained from *E. coli* Genetic Stock Center (Yale University), by means of the P1 transduction method, tolC::Tn10 was transferred to the BL21star (DE3) strain. In a word, the *E. coli* CAG12184 strain was cultured in the L-medium (1% polypeptone, 0.5% yeast extract, 0.5% sodium chloride, pH 7.2) containing 2.5mM calcium chloride, and 0.2 mL of the culture solution was added with the P1 phage and cultured at 37° C. for 10 minutes. This reaction solution was added to the soft agar (1% polypeptone, 0.5% yeast extract, 0.5% sodium chloride, 0.3% agar, 2.5mM calcium chloride, pH 7.2) preheated at 45° C., and seeded on the L-agar medium (1% polypeptone, 0.5% yeast extract, 0.5% sodium chloride, 1.8% agar, pH 7.2) containing 2.5mM calcium chloride. The resulting medium was cultured at 37° C. for 18 hours and then added with 3 mL of the L-medium, the soft agar was crushed, and the supernatant was collected to give the tolC-phage solution. Then the *E. coli* BL21star (DE3) strain (Invitrogen Co.) was cultured in the L-medium containing 2.5mM calcium chloride, and 0.1 ml of the culture solution was added with the tolC-phage solution and cultured at 37° C. for 10 minutes. Then the bacterial body was collected by centrifugation, added with 1 ml of the L-medium, cultured at 37° C. for 10 minutes, and seeded on the L-medium containing 10 μg/mL of tetracycline. After culturing at 37° C. for 18 hours, the emerged colonies were given as the BIstarTolC strain. The BIstarTolC strain is a tolC disrupted strain with deficiency of the TolC function.

Example 2

Construction of the E. coli acrAB Disrupted Strain

In the same way, from the *E. coli* JA300A strain having *E. coli* JA300A (acrAB::cat) described in Non Patent Literature 5, acrAB::cat was transferred to the BL21star (DE3) strain by the P1 transduction method, and selection was made with the L-agar medium containing of 5 μg/mL of chloramphenicol to give the BIstarAcRAB strain. Also, acrAB::cat was transferred to the BLstarTolC strain to give the BLstarTolCAcrAB strain. The BLstarAcRAB strain is an acrAB disrupted strain with deficiency of the AcrA function and the AcrB function. The BLstarTolCAcrAB strain is a TolC, acrAB disrupted strain additionally with the deficiency of the TolC function.

Example 3

Construction of Various Plasmids (1) pETAciBC-SD Vector

Hereinafter all the PCR reactions were carried out with KOD#PLUS-DNA polymerase (Toyobo Co., Ltd.). The plasmid pDolABC (see Non Patent Literature 6) was treated with the restriction enzymes NcoI and BamHI to give a DNA fragment containing the aciB gene (see Nucleotide No. 1 to 321 in SEQ ID No. 3) which encodes ferredoxin originated from the *Acinetobacter* sp. OC4 strain. This fragment was joined to the NcoI and BamHI sites of a *E. coli* plasmid vector, pETduet-1 (Novagen), by T4 DNA ligase to give Plasmid A. Moreover, PCR was carried out using Primer A (see SEQ ID No. 6) and Primer B (see SEQ ID No. 7), and pDolABC as a template to amplify the DNA fragment containing the gene aciC (see Nucleotide No. 1978 to 3192 of SEQ ID No. 3) which encodes ferredoxin reductase originated from the *Acinetobacter* sp. OC4 strain, and the treatment was performed with the restriction enzymes BamHI and HindIII. This fragment was joined to the BamHI and HindIII sites of Plasmid A by T4 DNA ligase to give Plasmid B. Then, in order to eliminate the rear one of the two T7 promoters of Plasmid B, Plasmid B was treated with the restriction enzymes EcoRV and NotI, smoothed using BKL Kit (Takara Shuzo Co., Ltd.), and then joined by T4 DNA ligase to give Plasmid C. On the other hand, PCR was carried out using Primer C (see SEQ ID No. 8) and Primer D (see SEQ ID No. 9), and the genomic DNA of the *Pseudonocardia autotrophica* ATCC33795 strain as a template to amplify the DNA fragment to be the spacer DNA sequence, and the treatment was performed with the restriction enzymes BglII and BamHI. This fragment was joined to the BglII and BamHI sites of Plasmid C by T4 DNA ligase to give pETAciBC-SD vector.

(2) Plasmid pETAciBC-50AABP195

PCR was carried out using Primer E (see SEQ ID No. 10) and Primer F (see SEQ ID No. 11), and the genomic DNA of the *Acinetobacter* sp. OC4 strain as a template to amplify the DNA fragment (the DNA fragment of from Nucleotide No. 398 to 541 of SEQ ID No. 3) which encodes the N-terminal site of the alkane oxidative P-450 enzyme AciA originated from the Acinetobacter sp. OC4 strain, and the treatment was performed with the restriction enzymes NdeI and SpeI. On the other hand, PCR was carried out using the primer BP195F (see SEQ ID No. 12) and the primer BP195R (see SEQ ID No. 13), and the genomic DNA of the *Dactylosporangium variesporum* IFO14104 strain as a template to amplify the BP195 gene (see Nucleotide No. 1 to 1203 of SEQ ID No. 2) which encodes the P-450 enzyme, and the treatment was performed with the restriction enzymes SpeI and BamHI. These DNA fragments were joined to the NdeI and BamHI sites of the pETAciBC-SD vector by T4 DNA ligase to give a plasmid, pETAciBC-50AABP195.

(3) Plasmid pETAciBC-50AAvdh

PCR was carried out using the primer vdhF (see SEQ ID No. 14) and the primer vdhR (see SEQ ID No. 15), and the genomic DNA of the *Pseudonocardia autotrophica* ATCC33795 strain as a template to amplify the vdh gene (see Nucleotide No. 320 to 1531 of SEQ ID No. 1) which encodes the P-450 enzyme, and the treatment was performed with the restriction enzymes SpeI and BglII. These DNA fragments were joined to the SpeI and BamHI sites of pETAciBC-50AABP195 by T4 DNA ligase to give a plasmid, pETAciBC-50AAvdh.

(4) Plasmid pETduet-boxA

The plasmid pETAciBC-SD vector was treated with the restriction enzymes BamHI and HindIII, and joined by T4 DNA ligase to the DNA fragment containing the gene aciC which encodes the protein sharing homology with ferredoxin reductase to give a plasmid, pETduetaciC. Then, using the primers boxBNcoF (see SEQ ID No. 16) and boxBBamR (see SEQ ID No. 17) and the genomic DNA of the *Streptomyces* sp. TM-7 strain, the DNA fragment containing the boxB gene (see Nucleotide No. 1782 to 1973 of SEQ ID No. 4) which encodes ferredoxin associated with the compactin oxidative P-450 enzyme was amplified, and the treatment was performed with the restriction enzymes NcoI and BamHI. This DNA fragment was joined by the T4 DNA ligase to pETduetaciC treated with the restriction enzymes NcoI and BamHI to give a plasmid, pETduetboxB. Moreover, using the primers boxANdeF (see SEQ ID No. 18) and boxAXhoR (see SEQ ID No. 19) and the genomic DNA of the *Streptomyces* sp. TM-7 strain, the DNA fragment containing the boxA gene (see Nucleotide No. 544 to 1761 of SEQ ID No. 4) which encodes the compactin oxidative P-450 enzyme was amplified, and the treatment was performed with the restriction enzymes NdeI and XhoI. This DNA fragment was joined by the T4 DNA ligase to pETduetboxB treated with the restriction enzymes NdeI and XhoI to give a plasmid, pETduet-boxA.

(5) Plasmid pTrcRat

PCR was carried out using the primer ExratF (see SEQ ID No. 20) and the primer ExratR (see SEQ ID No. 21), and the genomic DNA of the *Burkholderia cepacia* 895-3 strain as a template to amplify the ratA gene (see Nucleotide No. 230 to 1330 of SEQ ID No. 5) which encodes (R)-α-methyltryptamine aminotransferase, and the treatment was performed with the restriction enzymes PstI and EcoRI. This DNA fragment was joined to the PstI and EcoRI sites of pTrcHisA (Invitrogen Co.) by T4 DNA ligase to give a plasmid pTrcRat.

(6) Plasmid pTrcRat

PCR was carried out using the primer latSacF (see SEQ ID No. 24) and the primer latXhoR (see SEQ ID No. 25), and the genomic DNA of the *Flavobacterium lutescens* IFO3084 strain as a template to amplify the lat gene (see SEQ ID No. 30) which encodes lysine aminotransferase, and the treatment was performed with the restriction enzymes SacI and XhoI. PCR was carried out using the primer ZARXhoF (see SEQ ID No. 26) and the primer ZARBamR (see SEQ ID No. 27), and the genomic DNA of the *Flavobacterium lutescens* IFO3084 strain as a template to amplify the zar gene (see SEQ ID No. 31) which encodes N-benzyloxycarbonyl-L-aminoazipic acid-delta-semialdehyde reductase, and the treatment was performed with the restriction eminzymes XhoI and BamHI. And then, PCR was carried out using the primer rocGBamF (see SEQ ID No. 28) and the primer rocGXbaR (see SEQ ID No. 29), and the genomic DNA of the *Bacillus subtilis* str.168 ATCC23857 strain as a template to amplify the rocG gene (see SEQ ID No. 32), and the treatment was performed with the restriction eminzymes SacI and XbaI. These three DNA fragments were joined to the SacI and XbaI sites of pHSG298 (Takara Bio Co.) by T4 DNA ligase to give a plasmid pHSG-ZAR inserted lat, zar, and rocG in this order.

Example 4

Microbial Conversion From Vitamin $D_3$ Into 25-hydroxyvitamin $D_3$

Using the plasmid pETAciBC-50AAvdh, the *E. coli* BLstarTolCAcrAB strain, BLstarTolC strain, BLstarAcrAB strain and BL21star(DE3) strain were subjected to transformation to give, respectively, BIstarTolCAcrAB/pETAciBC-50AAvdh strain, BLstarTolC/pETAciBC-50AAvdh strain, BLstarAcrAB/pETAciBC-50AAvdh strain and BL21star/pETAciBC-50AAvdh strain. In the same way, using the plasmid pETAciBC-50AABP195, the *E. coli* BLstarTolCAcrAB strain, BLstarTolC strain, BLstarAcrAB strain and BL2lstar (DE3) strain were subjected to transformation to give, respectively, BIstarTolCAcrAB/pETAciBC-50AABP195 strain, BLstarTolC/pETAciBC-50AABP195 strain, BLstarAcrAB/pETAciBC-50AABP195 strain and BL21star/pETAciBC-50AABP195 strain. These strains were seeded in the M9SEED liquid medium (3.39% $Na_2HPO_4$, 1.5% $KH_2PO_4$, 0.25% calcium chloride, 0.5% ammonium chloride, 1% casamino acid, 0.002% thymine, 0.1mM calcium chloride, 0.1mM iron sulfate, 0.4% glucose, 0.001mM magnesium chloride) containing sodium carbenicillin (100 µg/mL), and cultured with shaking at 220 rpm at 25° C. for 24 hours. This culture solution 200 µL was added to 25 mL of the M9Main liquid medium (3.39% $Na_2HPO_4$, 1.5% $KH_2PO_4$, 0.25% sodium chloride, 0.5% ammonium chloride, 1% casamino acid, 0.002% thymine, 0.1mM calcium chloride, 0.1mM iron sulfate, 80 µg/mL 5-aminolevulinic acid) containing sodium carbenicillin (100 µg/mL) and Overnight Express Autoinduction Systems (Novagen), and cultured with shaking at 220 rpm at 25° C. for 24 hours. The bacterial body was collected by centrifugation, and suspended in 5 mL of the CV2 buffer (50mM potassium phosphate buffer, 2% glycerin, 50 µg/mL carbenicillin, 0.1M IPTG) to obtain the bacterial body suspension in the 5-times concentration to the culture solution. To 1 mL of this bacterial body suspension, 25 µL of 1% vitamin $D_3$ DMSO solution (the final concentration 250 µg/mL) and partially methylated cyclodextrin (the final concentration 0.75%) were added, and the resulting solution was cultured with shaking at 220 rpm at 28° C. for 24 hours. Then, the reaction mixture was added with 2 mL of methanol, vortexed at room temperature for 10 minutes, and then subjected to centrifugation by the Eppendorf centrifuge at 15,000 rpm for 10 minutes, and the resulting supernatant was analyzed by HPLC to detect 25-hydroxyvitamin $D_3$ generated by hydroxylating the substrate vitamin $D_3$. The result was shown in Table 1.

TABLE 1

| Host *E. coli* | Gene used for microbial conversion and accumulation concentration of vitamin $D_3$ hydroxylated product (µg/mL) | | Gene used for microbial conversion and specific activity to the wild strain | |
|---|---|---|---|---|
| | vdh | BP195 | vdh | BP195 |
| Wild strain | 46.7 | 13.0 | 1.0 | 1.0 |
| acrAB disrupted strain | 135.1 | 23.5 | 2.9 | 1.8 |
| tolC disrupted strain | 187.0 | 30.2 | 4.0 | 2.3 |
| tolC, acrAB disrupted strain | 216.4 | 38.7 | 4.6 | 3.0 |

The measurement conditions of HPLC were as follows:

| | |
|---|---|
| Analyzer: | AGILENT 100 series |
| Column: | J' SPHERE ODS-H80 (YMC, Inc.), 75 mm × 4.6 mm I.D. |
| Mobile phase: | A; acetonitrile |
| | B; ion-exchanged water |
| Gradient time setting: | 0 minute — mobile phase A/B = 30:70 |
| | 13.00 minutes — mobile phase A/B = 30:70 |
| | 14.00 minutes — mobile phase A/B = 100:0 |
| | 21.00 minutes — mobile phase A/B = 100:0 |
| | 22.00 minutes — mobile phase A/B = 70:30 |
| | 25.00 minutes — mobile phase A/B = 70:30 |
| Flow rate: | 1.0 mL/minute |
| Detection: | UV 265 nm |
| Injection volume: | 10 µL |
| Column temperature: | 40° C. |
| Analysis time: | 25 minutes |
| Retention time: | 25-hydroxyvitamin $D_3$ — 8.8 minutes |
| | Vitamin $D_3$ — 21.0 minutes |

In the microbial conversion of vitamin $D_3$ using the *E. coli* which had been caused to express the vdh gene encoding Vdh which is a P-450 enzyme and the aciAB gene encoding the electron transport system, in comparison with the case using the wild-type *E. coli* as the expression host for the conventional method, there showed 2.9 times accumulation of 25-hydroxyvitamin $D_3$ when using the acrAB disrupted strain, 4.0 times when using the tolC disrupted strain, and 4.6 times when using the tolCacrAB disrupted strain.

Also in the microbial conversion of vitamin $D_3$ using the *E. coli* which had been caused to express the gene encoding BP195 which is a P-450 enzyme and the aciAB gene encoding the electron transport system, in comparison with the case using the wild-type *E. coli* as the expression host for the conventional method, there showed 1.8 times accumulation of 25-hydroxyvitamin $D_3$ when using the acrAB disrupted strain, 2.3 times when using the tolC disrupted strain, and 3.0 times when using the tolCacrAB disrupted strain.

Example 5

Microbial Conversion from 4-cholesten-3-one into 25-hydroxy-4-cholesten-3-one Using the aforementioned E. coli BlstarTolCAcrAB/pET-AciBC-50AABP195 strain, BLstarTolC/pETAciBC-50AABP195 strain, BLstarAcrAB/pETAciBC-50AABP195 strain and BL21star/pETAciBC-50AABP195 strain, the bacterial body suspension was prepared in the same manner as in Example 4. To 1 mL of this bacterial body suspension, 25 μL of 1% 4-cholesten-3-one methanol solution (the final concentration 250 μg/mL) and partially methylated cyclodextrin (the final concentration 0.75%) were added, and the resulting solution was cultured with shaking at 220 rpm at 28° C. for 24 hours. Then, the reaction mixture was added with 2 mL of methanol, vortexed at room temperature for 10 minutes, and then subjected to centrifugation by the Eppendorf centrifuge at 15,000 rpm for 10 minutes, and the resulting supernatant was analyzed by HPLC to detect 25-hydroxy-4-cholesten-3-one generated by hydroxylating the substrate 4-cholesten-3-one. The result was shown in Table 2.

TABLE 2

| Host E. coli | Gene used for microbial conversion and accumulation concentration of 4-cholesten-3-one hydroxylated product (μg/mL) BP195 | Gene used for microbial conversion and specific activity to the wild strain BP195 |
| --- | --- | --- |
| Wild strain | 14.1 | 1.0 |
| acrAB disrupted strain | 19.9 | 1.4 |
| tolC disrupted strain | 151.0 | 10.5 |
| tolC, acrAB disrupted strain | 155.5 | 11.0 |

The measurement conditions of HPLC were as follows:

| | |
| --- | --- |
| Analyzer: | AGILENT 100 series |
| Column: | INERTSUL ODS/3 50 mm × 4.6 mm I.D. |
| Mobile phase: | A; acetonitrile<br>B; 0.85% aqueous phosphate solution |
| Gradient time setting: | 0 minute — mobile phase A/B = 40:60<br>5.00 minutes — mobile phase A/B = 100:0<br>8.00 minutes — mobile phase A/B = 100:0<br>8.30 minutes — mobile phase A/B = 40:60<br>11.00 minutes — mobile phase A/B = 40:60 |
| Flow rate: | 1.2 mL/minute |
| Detection: | UV 235 nm |
| Injection volume: | 40 μL |
| Column temperature: | 40° C. |
| Analysis time: | 11 minutes |
| Retention time: | 25-hydroxy-4-cholesten-3-one 4.97 minutes<br>4-cholesten-3-one 7.45 minutes |

Also in the microbial conversion of 4-cholesten-3-one, in comparison with the case using the wild-type E. coli as the expression host for the conventional method, there showed 1.4 times accumulation of 25-hydroxy-4-cholesten-3-one when using the acrAB disrupted strain, 10.5 times when using the tolC disrupted strain, and 11.0 times when using the tolCacrAB disrupted strain.

Example 6

Microbial Conversion from Compactin into Pravastatin

Using the aforementioned plasmid pETduet-boxA, the E. coli BLstarTolCAcrAB strain and BL21star(DE3) were subjected to transformation to give the BlstarTolCAcrAB/pETduet-boxA strain and BL21star/pETduet-boxA strain, respectively. Using these bacterial strains, the bacterial body suspension was prepared in the same manner as in Example 4. To 1 mL of this bacterial body suspension, 30 μL of 25 mg/mL compactin (the final concentration 750 μg/mL) was added, and the resulting solution was cultured with shaking at 220 rpm at 28° C. for 8 hours. Moreover, 30 μL of 25 mg/mL compactin was supplementary added (the final concentration 1500 μg/mL), and the resulting solution was cultured with shaking at 220 rpm at 28° C. for 16 hours. Then, the reaction mixture was added with 1 mL of methanol and 1 mL of acetonitrile, vortexed at room temperature for 10 minutes, and then subjected to centrifugation by the Eppendorf centrifuge at 15,000 rpm for 10 minutes, and the resulting supernatant was analyzed by HPLC to detect pravastatin generated by hydroxylating the substrate compactin. The result was shown in Table 3.

TABLE 3

| Host E. coli | Gene used for microbial conversion and accumulation concentration of compactin hydroxylated product (μg/mL) boxA | Gene used for microbial conversion and specific activity to the wild strain boxA |
| --- | --- | --- |
| Wild strain | 51.1 | 1.0 |
| acrAB disrupted strain | NT | NT |

TABLE 3-continued

| Host E. coli | Gene used for microbial conversion and accumulation concentration of compactin hydroxylated product (µg/mL) boxA | Gene used for microbial conversion and specific activity to the wild strain boxA |
|---|---|---|
| tolC disrupted strain | NT | NT |
| tolC, acrAB disrupted strain | 1689.0 | 33.1 |

The measurement conditions of HPLC were as follows:

| Analyzer: | AGILENT 100 series | |
|---|---|---|
| Column: | CHROMOLITH Performance RP-18e 100 mm × 4.6 mm I.D. | |
| Mobile phase: | A; methanol:triethylamine:acetic acid = 100:0.1:0.1 B; water:triethylamine:acetic acid = 100:0.1:0.1 | |
| Gradient time setting: | 0 minute | mobile phase A/B = 50:50 |
| | 3.00 minutes | mobile phase A/B = 90:10 |
| | 3.50 minutes | mobile phase A/B = 90:10 |
| | 3.51 minutes | mobile phase A/B = 40:50 |
| | 5.00 minutes | mobile phase A/B = 50:50 |
| Flow rate: | 2.0 mL/minute | |
| Detection: | UV 238 nm | |
| Injection volume: | 15 uL | |
| Column temperature: | 40° C. | |
| Analysis time: | 6 minutes | |
| Retention time: | pravastatin | 1.77 minutes |
| | compactin | 3.23 minutes |

Also in the microbial conversion of compactin using the *E. coli* which had been caused to express the gene encoding BoxA which is a P-450 enzyme and the boxB and aciC genes encoding its electron transport system, in comparison with the case using the wild-type *E. coli* as the expression host for the conventional method, there showed accumulation of 33.1 times of pravastatin when using the tolCacrAB disrupted strain.

Example 7

Microbial Conversion from (R)-α-methyltryptamine into indole-3-acetone

Using the aforementioned plasmid pTrcRat, the *E. coli* BLstarTolCAcrAB strain and BL21star(DE3) strain were subjected to transformation to give the BlstarTolCAcrAB/pTrcRat strain and BL21star/pTrcRat strain, respectively. These strains were seeded in the L liquid medium (1.0% polypeptone, 0.5% yeast extract, 0.5% sodium chloride, pH 7.2) containing sodium carbenicillin (100 µg/mL), and cultured with shaking at 220 rpm at 37° C. for 8 hours. This culture solution 50 µL was added to 25 ml of the L liquid medium containing sodium carbenicillin (100 µg/mL) and Overnight Express Autoinduction Systems (Novagen), and cultured with shaking at 220 rpm at 30° C. for 20 hours. The bacterial body was collected by centrifugation, and suspended in 2.5 ml of the borate buffer (200mM, pH 9.0) to obtain the bacterial body suspension in the 10-times concentration to the culture solution. To 0.5 mL of this bacterial body suspension, 0.5 mL of the L liquid medium, 25 µL of 50% glycerol solution, 1.25 µL of 50 mg/mL sodium carbenicillin, 10 µL of 100mM IPTG, and 250 µL of 25mM (R)-α-methyltryptamine were added, and the resulting solution was cultured with shaking at 220 rpm at 30° C. for 18 hours. Then, the reaction mixture was added with 50 µL of 5N sodium hydroxide solution and 2 mL of ethyl acetate, vortexed at room temperature for 10 minutes, and then subjected to centrifugation by the Eppendorf centrifuge at 15,000 rpm for 10 minutes, and the resulting supernatant was concentrated to dryness, and dissolved in 300 µL of methanol. The resulting solution was analyzed by HPLC to detect indole-3-acetone generated by dissociating the amino group from the substrate (R)-α-methyltryptamine (R-MT). The result was shown in Table 4.

TABLE 4

| Host E. coli | Gene used for microbial conversion and accumulation concentration of R-MT hydroxylated product (µg/mL) ratA | Gene used for microbial conversion and specific activity to the wild strain ratA |
|---|---|---|
| Wild strain | 81.6 | 1.0 |
| acrAB disrupted strain | NT | NT |
| tolC disrupted strain | NT | NT |
| tolC, acrAB disrupted strain | 97.8 | 1.2 |

The measurement conditions of HPLC were as follows:

| Analyzer: | AGILENT 100 series | |
|---|---|---|
| Column: | CHILALPAK AS-H (DAICEL) 250 mm × 4.6 mm I.D. | |
| Mobile phase: | hexane:isopropyl alcohol:diethylamine = 75:25:0.6 | |
| Flow rate: | 0.7 mL/minute | |
| Detection: | UV 238 nm | |
| Injection volume: | 15 µL | |
| Column temperature: | 25° C. | |
| Analysis time: | 15 minutes | |
| Retention time: | (R)-α-methyltryptamine | 6.5 minutes |
| | indole-3-acetone | 11.4 minutes |

In the microbial conversion of (R)-α-methyltryptamine using the *E. coli* which had been caused to express the gene encoding RatA which is a (R)-α-methyltryptamine aminotransferase, in comparison with the case using the wild-type *E. coli* as the expression host for the conventional method, there showed 1.2 times accumulation of indole-3-acetone when using the tolCacrAB disrupted strain.

Example 8

Microbial Conversion from N-benzyloxycarbonyl-L-lysine (Z-Lys) into N-benzyloxycarbonyl-6-hydroxy-L-norleucine (Z-HNL)

Z-Lys is converted into N-benzyloxycarbonyl-L-aminoazipic acid-delta-semialdehyde (L-ASA) by lysine aminotransferase encoded by the lat gene in the plasmid pHSG-ZAR, Z-ASA is converted into Z-HNL by a Z-ASA reductase encoded by the zar gene, a coenzyme NADPH is regenerated by glutaminic acid dehydrogenase encoded by the rocG gene. Using the plasmid pHSG-ZAR, the *E. coli* BLstarTolCAcrAB strain and BL21star(DE3) strain were subjected to transformation to give, respectively, BIstarTolCAcrAB/pHSG-ZAR strain and BL21star/pHSG-ZAR strain. These strains were seeded in the M9SEED liquid medium (3.39% $Na_2HPO_4$, 1.5% $KH_2PO_4$, 0.25% calcium chloride, 0.5% ammonium chloride, 1% casamino acid, 0.002% thymine, 0.1mM calcium chloride, 0.1mM iron sulfate, 0.4% glucose, 0.001mM magnesium chloride) containing kanamycin sulfate (25 μg/mL), and cultured with shaking at 220 rpm at 25° C. for 24 hours. This culture solution 200 μL was added to 25 mL of the M9ZAR liquid medium (3.39% $Na_2HPO_4$, 1.5% $KH_2PO_4$, 0.25% sodium chloride, 0.5% ammonium chloride, 1% casamino acid, 0.002% thymine, 0.1mM calcium chloride) containing kanamycin sulfate (80 μg/mL) and Overnight Express Autoinduction Systems (Novagen), and cultured with shaking at 220 rpm at 30° C. for 7 hours and then cultured with shaking at 140 rpm at 25° C. for 17 hours. The bacterial body was collected by centrifugation, and suspended in 5 mL of the CV3 buffer (50mM potassium phosphate buffer, 2% glycerin, 20 μg/mL kanamycin sulfate, 0.1M IPTG) to obtain the bacterial body suspension in the 5-times concentration to the culture solution. To 1 mL of this bacterial body suspension, 40 μL of 25 mg/mL Z-Lys solution (the final concentration 1000 μg/mL) and γ-cyclodextrin (the final concentration 2%) were added, and the resulting solution was cultured with shaking at 220 rpm at 28° C. for 24 hours. Then, the reaction mixture was added with 2 mL of methanol, vortexed at room temperature for 10 minutes, and then subjected to centrifugation by the Eppendorf centrifuge at 15,000 rpm for 10 minutes, and the resulting supernatant was analyzed by HPLC to detect Z-HNL converted from the substrate Z-Lys. The result was shown in Table 5.

TABLE 5

| Host *E. coli* | Gene used for microbial conversion and Z-HNL accumulation concentration (μg/mL) lat, zar, rocG | Gene used for microbial conversion and specific activity to the wild strain lat, zar, rocG |
|---|---|---|
| Wild strain | 288 | 1 |
| acrAB disrupted strain | N.T. | N.T. |
| tolC disrupted strain | N.T. | N.T. |
| tolC, acrAB disrupted strain | 420 | 1.5 |

The measurement conditions of HPLC were as follows:

| | |
|---|---|
| Analyzer: | AGILENT 100 series |
| Column: | J' SPHERE ODS-H80 (YMC, Inc.), 75 mm × 4.6 mm I.D. |
| Mobile phase: | A; acetonitrile B; 0.85% aqueous phosphate solution |
| Gradient time setting: | 0 minute   mobile phase A/B = 20:80 6.00 minutes   mobile phase A/B = 20:80 8.00 minutes   mobile phase A/B = 60:40 10.00 minutes   mobile phase A/B = 20:80 |
| Flow rate: | 1.5 mL/minute |
| Detection: | UV 220 nm |
| Injection volume: | 10 μL |
| Column temperature: | 40° C. |
| Analysis time: | 10 minutes |
| Retention time: | Z-HNL   3.1 minutes |

In the microbial conversion of Z-Lys using the *E. coli* which had been caused to express the genes respectively encoding lysine aminotransferase, N-benzyloxycarbonyl-L-aminoazipic acid-delta-semialdehyde reductase and glutaminic acid dehydrogenase, in comparison with the case using the wild-type *E. coli* as the expression host for the conventional method, there showed 1.5 times accumulation of Z-HNL when using the tolCacrAB disrupted strain.

[Industrial Applicability]

The present invention is useful in the compound manufacturing domain utilizing microbial conversion.

The invention claimed is:

1. A transformant obtainable by the process comprising introducing (a) a gene originated from a xenogeneic organism encoding an enzyme selected from the group consisting of cytochrome P-450 enzyme categorized into family CYP105 and cytochrome P-450 enzyme categorized into family CYP107 into (b) E. coli defective in a gene encoding multi drug efflux protein and selected from the group consisting of tolC and acrAB.

2. A method of microbial conversion which uses the transformant according to claim 1.

3. A method of microbial conversion according to claim 2, characterized by performing monooxygenation to a substrate compound.

4. The method according to claim 3, wherein the substrate compound is selected from the group consisting of vitamin $D_3$, 4-cholesten-3-one, and compactin.

* * * * *

SEQUENCE LISTING

<160> NUMBER OF SEQ ID NOS: 24

<210> SEQ ID NO 1
<211> LENGTH: 50
<212> TYPE: PRT
<213> ORGANISM: Acinetobacter sp. OC4

<400> SEQUENCE: 1

Met Asn Ser Val Ala Glu Ile Phe Glu Lys Ile Thr Gln Thr Val Thr
1               5                   10                  15

Ser Thr Ala Ala Asp Val Ala Thr Thr Val Thr Asp Lys Val Lys Ser
            20                  25                  30

```
Asn Glu Gln Phe Gln Thr Gly Lys Gln Phe Leu His Gly Gln Val Thr
            35                  40                  45
Thr Ser
    50

<210> SEQ ID NO 2
<211> LENGTH: 3192
<212> TYPE: DNA
<213> ORGANISM: Acinetobacter sp. OC4
<220> FEATURE:
<221> NAME/KEY: CDS
<222> LOCATION: (1)..(318)
<223> OTHER INFORMATION: aciB
<220> FEATURE:
<221> NAME/KEY: CDS
<222> LOCATION: (398)..(1888)
<223> OTHER INFORMATION: aciA
<220> FEATURE:
<221> NAME/KEY: CDS
<222> LOCATION: (1978)..(3189)
<223> OTHER INFORMATION: aciC

<400> SEQUENCE: 2 atg ggc caa att aca ttt att gcc cac gat ggt gca caa acc agc gtt      48
Met Gly Gln Ile Thr Phe Ile Ala His Asp Gly Ala Gln Thr Ser Val
  1               5                  10                  15 gca atc gaa gcg ggt aag tca cta atg cag ttg gcg gtt gaa aac ggt      96
Ala Ile Glu Ala Gly Lys Ser Leu Met Gln Leu Ala Val Glu Asn Gly
             20                  25                  30 gtt gcc gga att gat ggg gat tgc ggt ggc gaa tgc gcc tgt ggt acc     144
Val Ala Gly Ile Asp Gly Asp Cys Gly Gly Glu Cys Ala Cys Gly Thr
         35                  40                  45 tgc cac gtg att gtc agt gct gag tgg tcg gat gtt gcg ggt acg gca     192
Cys His Val Ile Val Ser Ala Glu Trp Ser Asp Val Ala Gly Thr Ala
     50                  55                  60 caa gcg aat gag cag cag atg ttg gaa atg acc cca gag cgt gct gcc     240
Gln Ala Asn Glu Gln Gln Met Leu Glu Met Thr Pro Glu Arg Ala Ala
 65                  70                  75                  80 acc tca cgt ttg gcg tgt tgt atc caa gtg acc gat gca atg gat ggc     288
Thr Ser Arg Leu Ala Cys Cys Ile Gln Val Thr Asp Ala Met Asp Gly
                 85                  90                  95 atg acg gta cat ctg cct gag ttt cag atg taa cacgtcagct gtaacccagc    341
Met Thr Val His Leu Pro Glu Phe Gln Met
                100                 105 ggatcaaccg ccttaacaaa cacacctcgt caacgatgct cagtcaggag accatc        397 atg aac tca gtc gca gaa att ttt gag aaa ata acc caa act gtc acc     445
Met Asn Ser Val Ala Glu Ile Phe Glu Lys Ile Thr Gln Thr Val Thr
                110                 115                 120 agc acc gct gca gac gta gca acc acg gtt acg gat aaa gtc aag tct     493
Ser Thr Ala Ala Asp Val Ala Thr Thr Val Thr Asp Lys Val Lys Ser
            125                 130                 135 aat gag cag ttt caa acg ggc aag cag ttt ttg cat ggt caa gtg acc     541
Asn Glu Gln Phe Gln Thr Gly Lys Gln Phe Leu His Gly Gln Val Thr
        140                 145                 150 cgt ttt gtc cca ttg cac acg cag gtt cgc ggc att cag tgg atg caa     589
Arg Phe Val Pro Leu His Thr Gln Val Arg Gly Ile Gln Trp Met Gln
155                 160                 165                 170 aaa gcc aaa ttc cgt gtg ttt aac gtg caa gaa ttt cct gca ttt atc     637
Lys Ala Lys Phe Arg Val Phe Asn Val Gln Glu Phe Pro Ala Phe Ile
                175                 180                 185 gag caa ccg att cca gaa gtt gca aca ctg gca ctt gct gag att gat     685
Glu Gln Pro Ile Pro Glu Val Ala Thr Leu Ala Leu Ala Glu Ile Asp
            190                 195                 200
```

```
gtt agc aac cca ttt tta tac aag caa aaa aaa tgg cag tct tac ttt      733
Val Ser Asn Pro Phe Leu Tyr Lys Gln Lys Lys Trp Gln Ser Tyr Phe
    205             210                 215 aag cgg ctg cgt gat gaa gca ccg gta cat tat caa gcc aac agt ccg      781
Lys Arg Leu Arg Asp Glu Ala Pro Val His Tyr Gln Ala Asn Ser Pro
220             225                 230 ttt ggg gca ttt tgg tcg gtc acg cgt tac gat gat att gtc tat gtc      829
Phe Gly Ala Phe Trp Ser Val Thr Arg Tyr Asp Asp Ile Val Tyr Val
235             240                 245                 250 gat aaa aat cat gag att ttt tca gct gaa cct gtg atc gcg att ggc      877
Asp Lys Asn His Glu Ile Phe Ser Ala Glu Pro Val Ile Ala Ile Gly
                255                 260                 265 aac acc cct cct ggg tta ggt gct gaa atg ttt att gca atg gac cca      925
Asn Thr Pro Pro Gly Leu Gly Ala Glu Met Phe Ile Ala Met Asp Pro
        270                 275                 280 ccc aag cac gat gtg cag cgg cag gcc gta cag gat gta gtc gca cca      973
Pro Lys His Asp Val Gln Arg Gln Ala Val Gln Asp Val Val Ala Pro
    285                 290                 295 aaa aat ctc aaa gag cta gag ggt ttg att cgg cta cgc gtg caa gag     1021
Lys Asn Leu Lys Glu Leu Glu Gly Leu Ile Arg Leu Arg Val Gln Glu
300                 305                 310 gtt ttg gat cag ttg cca acg gat cag ccg ttt gat tgg gtg cag aat     1069
Val Leu Asp Gln Leu Pro Thr Asp Gln Pro Phe Asp Trp Val Gln Asn
315             320                 325                 330 gtt tcg att gag ctg aca gcc cgt atg ttg gca aca tta ttt gat ttc     1117
Val Ser Ile Glu Leu Thr Ala Arg Met Leu Ala Thr Leu Phe Asp Phe
                335                 340                 345 cca tac gaa aag cgg cac aaa ttg gtt gaa tgg tca gac ttg atg gct     1165
Pro Tyr Glu Lys Arg His Lys Leu Val Glu Trp Ser Asp Leu Met Ala
        350                 355                 360 ggc act gcg gag gcc aca ggt ggg aca gtg aca aat ttg gat gag att     1213
Gly Thr Ala Glu Ala Thr Gly Gly Thr Val Thr Asn Leu Asp Glu Ile
    365                 370                 375 ttt gat gca gca gtc gat gca gca aag cat ttt gcg gag tta tgg cat     1261
Phe Asp Ala Ala Val Asp Ala Ala Lys His Phe Ala Glu Leu Trp His
380                 385                 390 aga aaa gcc gca caa aaa tct gca ggc gct gaa atg ggc tat gat ttg     1309
Arg Lys Ala Ala Gln Lys Ser Ala Gly Ala Glu Met Gly Tyr Asp Leu
395             400                 405                 410 atc agc ttg atg cag tca aac gaa gcg act aaa gac ctg att tat cgg     1357
Ile Ser Leu Met Gln Ser Asn Glu Ala Thr Lys Asp Leu Ile Tyr Arg
                415                 420                 425 ccg atg gag ttt atg ggc aat ttg gtc ttg cta att gtc ggc ggc aac     1405
Pro Met Glu Phe Met Gly Asn Leu Val Leu Leu Ile Val Gly Gly Asn
        430                 435                 440 gat acc aca cgc aac tcg atg acg ggt ggg gta tac gca ctt aac ctg     1453
Asp Thr Thr Arg Asn Ser Met Thr Gly Gly Val Tyr Ala Leu Asn Leu
    445                 450                 455 ttt cca aat gag ttc gtc aaa ctc aaa aac aat ccg agc ttg atc ccg     1501
Phe Pro Asn Glu Phe Val Lys Leu Lys Asn Asn Pro Ser Leu Ile Pro
460                 465                 470 aac atg gta tcc gaa att att cgc tgg caa acc ccg ctg gcc tat atg     1549
Asn Met Val Ser Glu Ile Ile Arg Trp Gln Thr Pro Leu Ala Tyr Met
475             480                 485                 490 cgt cgg att gcc aag caa gat gta gag ctt aac ggt cag acc atc aaa     1597
Arg Arg Ile Ala Lys Gln Asp Val Glu Leu Asn Gly Gln Thr Ile Lys
                495                 500                 505 aaa ggc gac aag gtg gtg atg tgg tac gtt tct ggc aac cgc gat gag     1645
Lys Gly Asp Lys Val Val Met Trp Tyr Val Ser Gly Asn Arg Asp Glu
        510                 515                 520
```

```
cga gtg att gag cga cct gat gaa ttg atc att gat cgt aaa ggt gcg       1693
Arg Val Ile Glu Arg Pro Asp Glu Leu Ile Ile Asp Arg Lys Gly Ala
        525                 530                 535 cgt aat cat ctg tca ttt ggt ttt ggt gtg cat cgc tgt atg ggt aat       1741
Arg Asn His Leu Ser Phe Gly Phe Gly Val His Arg Cys Met Gly Asn
540                 545                 550 cgc ttg gcc gag atg cag ttg cga atc tta tgg gaa gag ctg ctt cag       1789
Arg Leu Ala Glu Met Gln Leu Arg Ile Leu Trp Glu Glu Leu Leu Gln
555                 560                 565                 570 cgt ttt gaa aat att gag gtt ttg ggt gag cca gaa att gtg caa tct       1837
Arg Phe Glu Asn Ile Glu Val Leu Gly Glu Pro Glu Ile Val Gln Ser
        575                 580                 585 aac ttt gtg cgc ggc tat gcc aag atg atg gtc aaa ctg act gcc aaa       1885
Asn Phe Val Arg Gly Tyr Ala Lys Met Met Val Lys Leu Thr Ala Lys
        590                 595                 600 gcg tag gtatcaaaat aggcgacaga ggcattttgc aactgtcgtc ggcaacgatt ga     1943
Ala tgctgtgcat caaccatgaa ctgagtgaat tcat atg caa aca atc gtc atc att     1998
                                     Met Gln Thr Ile Val Ile Ile
                                                 605             610 ggc gca agt cat gct gcg gcg cag ttg gcg gca agt ctg cgg cca gat       2046
Gly Ala Ser His Ala Ala Ala Gln Leu Ala Ala Ser Leu Arg Pro Asp
                615                 620                 625 ggc tgg cag ggc gag att gtg gtg atc ggc gat gag ccg tat ttg ccg       2094
Gly Trp Gln Gly Glu Ile Val Val Ile Gly Asp Glu Pro Tyr Leu Pro
                630                 635                 640 tat cat cga ccg ccg ttg tcc aag acc ttt tta cgc ggt gca caa ctg       2142
Tyr His Arg Pro Pro Leu Ser Lys Thr Phe Leu Arg Gly Ala Gln Leu
        645                 650                 655 gtc gat gag tta ttg att cgg cca gcc gct ttt tat caa aaa aat cag       2190
Val Asp Glu Leu Leu Ile Arg Pro Ala Ala Phe Tyr Gln Lys Asn Gln
660                 665                 670 atc gaa ttt cgg cac ggg cgg gtg gtt gcg att gat cgg gca gcg cgc       2238
Ile Glu Phe Arg His Gly Arg Val Val Ala Ile Asp Arg Ala Ala Arg
675                 680                 685                 690 agc gtg aca cta caa gat ggc agt acg ctt gcg tat gac cag ttg gcg       2286
Ser Val Thr Leu Gln Asp Gly Ser Thr Leu Ala Tyr Asp Gln Leu Ala
                695                 700                 705 ctg tgt acc ggt gca cga gtc agg acg gtg tcg ctg gct ggg tct gat       2334
Leu Cys Thr Gly Ala Arg Val Arg Thr Val Ser Leu Ala Gly Ser Asp
                710                 715                 720 ttg gca ggt gtg cat tat ctt aga aat atc agc gat gta cag gct atc       2382
Leu Ala Gly Val His Tyr Leu Arg Asn Ile Ser Asp Val Gln Ala Ile
        725                 730                 735 cag cca ttt gta caa ccc aac ggc aaa gca gtg gtg atc ggt ggt ggc       2430
Gln Pro Phe Val Gln Pro Asn Gly Lys Ala Val Val Ile Gly Gly Gly
        740                 745                 750 tat atc ggt ctt gaa aca gcc gcc gca ttg acc gag cag ggc atg cag       2478
Tyr Ile Gly Leu Glu Thr Ala Ala Ala Leu Thr Glu Gln Gly Met Gln
755                 760                 765                 770 gtg gtg gtc ttg gaa gcc gcc gag cgg att ttg cag cgg gta act gca       2526
Val Val Val Leu Glu Ala Ala Glu Arg Ile Leu Gln Arg Val Thr Ala
                775                 780                 785 ccg gaa gtg tcg gac ttt tat acg cgg att cat cgc gaa cag ggt gtg       2574
Pro Glu Val Ser Asp Phe Tyr Thr Arg Ile His Arg Glu Gln Gly Val
                790                 795                 800 acg att cat acc ggt gtg tcg gtc acg gcg atc acg ggt gag ggg cgg       2622
Thr Ile His Thr Gly Val Ser Val Thr Ala Ile Thr Gly Glu Gly Arg
                805                 810                 815 gcg cag gcg gtg ctg tgt gcc gat ggt tcg atg ttc gat gca gat ctg       2670
```

-continued

```
            Ala Gln Ala Val Leu Cys Ala Asp Gly Ser Met Phe Asp Ala Asp Leu
                820                 825                 830 gtg atc atc ggg gtc ggg gtt gta ccg aat atc gag ttg gcg ctg gac      2718
Val Ile Ile Gly Val Gly Val Val Pro Asn Ile Glu Leu Ala Leu Asp
835                 840                 845                 850 gcg ggc ttg cag gtg gac aat ggt att gtg att gat gag tat tgc cga      2766
Ala Gly Leu Gln Val Asp Asn Gly Ile Val Ile Asp Glu Tyr Cys Arg
                855                 860                 865 acc agt gcg cca gag att gtg gcc atc ggg gat tgt gcc aat gcg ttt      2814
Thr Ser Ala Pro Glu Ile Val Ala Ile Gly Asp Cys Ala Asn Ala Phe
            870                 875                 880 aat ccg att tat cag cgg cgg atg cgc ttg gag tcg gta cca aac gcc      2862
Asn Pro Ile Tyr Gln Arg Arg Met Arg Leu Glu Ser Val Pro Asn Ala
        885                 890                 895 aat gaa cag gcc aaa att gcc tcg gcg acc ttg tgt ggc tta cag cgg      2910
Asn Glu Gln Ala Lys Ile Ala Ser Ala Thr Leu Cys Gly Leu Gln Arg
    900                 905                 910 acc tcg aag agt ttg cct tgg ttt tgg tca gat cag tat gat cta aag      2958
Thr Ser Lys Ser Leu Pro Trp Phe Trp Ser Asp Gln Tyr Asp Leu Lys
915                 920                 925                 930 ttg cag att gcg gga ctc agt cag ggg tat gat cag atc gtg att cgg      3006
Leu Gln Ile Ala Gly Leu Ser Gln Gly Tyr Asp Gln Ile Val Ile Arg
                935                 940                 945 ggt gat gtg cag caa agg cgt agc ttt gca gcg ttt tat ttg cag gcg      3054
Gly Asp Val Gln Gln Arg Arg Ser Phe Ala Ala Phe Tyr Leu Gln Ala
            950                 955                 960 ggt cgc ctg att gcg gcg gat tgt gtg aat cgt ccg cag gag ttt atg      3102
Gly Arg Leu Ile Ala Ala Asp Cys Val Asn Arg Pro Gln Glu Phe Met
        965                 970                 975 cta agc aaa aag ctg atc acg gct ggt acg gcg gtc gat cca ctg cgg      3150
Leu Ser Lys Lys Leu Ile Thr Ala Gly Thr Ala Val Asp Pro Leu Arg
    980                 985                 990 ttg gcg gat gag tcg att gcg gta cag gcg ttg atg ggg tag             3192
Leu Ala Asp Glu Ser Ile Ala Val Gln Ala Leu Met Gly
995                 1000                1005

<210> SEQ ID NO 3
<211> LENGTH: 2011
<212> TYPE: DNA
<213> ORGANISM: Pseudonocardia autotrophica ATCC33795
<220> FEATURE:
<221> NAME/KEY: CDS
<222> LOCATION: (320)..(1528)
<223> OTHER INFORMATION: vdh

<400> SEQUENCE: 3
gcgctcgggc tggaccggat cggcgaggtg acgacgctgg ggctgcgctc ggtgcggacc       60
gcatgggccg ggctgcggac gttcgccccg gaccgggccc cggtgctggg ggagtggccc      120
gatcatcccg ggttccactt cgtcgccggc cagggtggat ccggtatcga gtcggctccg      180
gcgctggccc cgctggcagc gtcgatgatc gtcgggcggc cggcgcccgc cgatgtcgcg      240
ctcgatcccg ctgtgtgctc ggtcactcgt ctccggtgac gtaagcgcgc gcttacgtcg      300
cgctggcacg atgggggccc atg gcg ctg acc acc acc ggc acc gag cag cac      352
                        Met Ala Leu Thr Thr Thr Gly Thr Glu Gln His
                         1               5                  10 gac ctg ttc tcg ggc acc ttc tgg cag aac ccg cat ccc gcc tac gcg       400
Asp Leu Phe Ser Gly Thr Phe Trp Gln Asn Pro His Pro Ala Tyr Ala
             15                  20                  25 gca ctc cgt gcc gag gat ccg gta cgc aag ctc gcg ctg ccg gac ggg       448
Ala Leu Arg Ala Glu Asp Pro Val Arg Lys Leu Ala Leu Pro Asp Gly
         30                  35                  40
```

```
ccg gtc tgg ctg ctc acc cgc tac gcc gac gtg cgc gag gcg ttc gtc      496
Pro Val Trp Leu Leu Thr Arg Tyr Ala Asp Val Arg Glu Ala Phe Val
    45                  50                  55 gat ccg cgc ctg tcg aag gac tgg cgc cac acg ctg ccc gag gac cag      544
Asp Pro Arg Leu Ser Lys Asp Trp Arg His Thr Leu Pro Glu Asp Gln
60                  65                  70                  75 cgg gcg gac atg ccg gcc acg ccg acg ccg atg atg atc ctg atg gat      592
Arg Ala Asp Met Pro Ala Thr Pro Thr Pro Met Met Ile Leu Met Asp
                80                  85                  90 ccg ccg gat cac acc cgg ctg cgc aag ctg gtc ggc agg tcg ttc acc      640
Pro Pro Asp His Thr Arg Leu Arg Lys Leu Val Gly Arg Ser Phe Thr
            95                  100                 105 gtc cgc cgg atg aac gag ctg gag ccg cgg atc acc gag atc gcc gac      688
Val Arg Arg Met Asn Glu Leu Glu Pro Arg Ile Thr Glu Ile Ala Asp
        110                 115                 120 ggc ctg ctc gcc ggc ctg ccc acc gac ggc ccg gtc gac ctg atg cgc      736
Gly Leu Leu Ala Gly Leu Pro Thr Asp Gly Pro Val Asp Leu Met Arg
125                 130                 135 gag tac gcg ttc cag atc ccg gta cag gtg atc tgc gag ctg ctc ggg      784
Glu Tyr Ala Phe Gln Ile Pro Val Gln Val Ile Cys Glu Leu Leu Gly
140                 145                 150                 155 gtg ccc gcc gag gac cgc gac gac ttc tcc gcg tgg tcg tcg gtg ctg      832
Val Pro Ala Glu Asp Arg Asp Asp Phe Ser Ala Trp Ser Ser Val Leu
                160                 165                 170 gtc gac gac tcg ccg gcc gac gac aag aac gcg gcc atg ggc aag ctg      880
Val Asp Asp Ser Pro Ala Asp Asp Lys Asn Ala Ala Met Gly Lys Leu
            175                 180                 185 cac ggc tac ctg tcc gac ctg ctg gag cgc aag cgc acc gag ccc gac      928
His Gly Tyr Leu Ser Asp Leu Leu Glu Arg Lys Arg Thr Glu Pro Asp
        190                 195                 200 gac gcg ctg ttg tcg tcg ctg ctg gcg gtg tcc gac gag gac ggc gac      976
Asp Ala Leu Leu Ser Ser Leu Leu Ala Val Ser Asp Glu Asp Gly Asp
205                 210                 215 cgg ctc tcc cag gag gag ctc gtc gcg atg gcg atg ctg ctg ctg atc     1024
Arg Leu Ser Gln Glu Glu Leu Val Ala Met Ala Met Leu Leu Leu Ile
220                 225                 230                 235 gcc ggg cac gag acg acg gtc aac ctg atc ggc aac ggc gtc ctc gcc     1072
Ala Gly His Glu Thr Thr Val Asn Leu Ile Gly Asn Gly Val Leu Ala
                240                 245                 250 ctg ctc acg cac ccc gac cag cgg aag ctg ctg gcc gag gac ccg tcg     1120
Leu Leu Thr His Pro Asp Gln Arg Lys Leu Leu Ala Glu Asp Pro Ser
            255                 260                 265 ctg atc agc tcg gcg gtc gag gag ttc ctg cgg ttc gac tct ccc gtc     1168
Leu Ile Ser Ser Ala Val Glu Glu Phe Leu Arg Phe Asp Ser Pro Val
        270                 275                 280 tcg cag gcc ccg atc cgg ttc acc gcg gag gac gtc acc tac tcc ggc     1216
Ser Gln Ala Pro Ile Arg Phe Thr Ala Glu Asp Val Thr Tyr Ser Gly
285                 290                 295 gtg acc atc ccg gcc ggc gag atg gtc atg ctc ggg ctg gcc gcc gcc     1264
Val Thr Ile Pro Ala Gly Glu Met Val Met Leu Gly Leu Ala Ala Ala
300                 305                 310                 315 aac cgg gac gcc gac tgg atg ccc gag ccg gac cgg ctc gac atc acc     1312
Asn Arg Asp Ala Asp Trp Met Pro Glu Pro Asp Arg Leu Asp Ile Thr
                320                 325                 330 cgg gac gcc tcc ggc ggg gtg ttc ttc ggg cac ggc atc cac ttc tgc     1360
Arg Asp Ala Ser Gly Gly Val Phe Phe Gly His Gly Ile His Phe Cys
            335                 340                 345 ctc ggt gcc cag ctg gcc cgg ctg gag ggc cgg gtc gcg atc gga cgg     1408
Leu Gly Ala Gln Leu Ala Arg Leu Glu Gly Arg Val Ala Ile Gly Arg
        350                 355                 360
```

```
ctg ttc gcc gat cgc ccg gag ctg gcg ctc gcg gtc ggc ctc gac gag     1456
Leu Phe Ala Asp Arg Pro Glu Leu Ala Leu Ala Val Gly Leu Asp Glu
365                 370                 375 ctg gtc tac cgg gag tcg acg ctg gtc cgg ggg ctg tcg agg atg ccg     1504
Leu Val Tyr Arg Glu Ser Thr Leu Val Arg Gly Leu Ser Arg Met Pro
380                 385                 390                 395 gtg acg atg ggg ccg cgc agc gcc tga tcccgttcgc ggacgggccg           1551
Val Thr Met Gly Pro Arg Ser Ala
                400 ggcggcccgt ccgcgagtac ggtcagccgc tcagtggtgc cccggtcttc tcccgcacct   1611
cgtcggcggt gacgccggga gcggtctcga ccagcgcgag gccgcccggg gtgacgtcga   1671
tgacggcgag atcggtgacg atccgggtga cgcagcccag cccggtgatg gcaggctgc    1731
acgactcgac gatcttgggc gtgccgtcgc gggacacgtg gtccatcatc acgatgacgg   1791
tgcgggcgcc gtgcacgagg tccatcgcgc cgcccatccc cttgatcatc ttcccgggca   1851
cggcccagtt ggcgagatcg ccgttggcgg cgacctgcat gccgccgagc acggacgt    1911
cgagcttccc ggcgcggatc tgggcgaagc tgtccgagga gccgaagtag cggcgccgt    1971
cgttgacggt gacggtctcc ttgcccgcgt tgatcaggtc                         2011

<210> SEQ ID NO 4
<211> LENGTH: 1203
<212> TYPE: DNA
<213> ORGANISM: Dactylosporangium variesporum IFO14104
<220> FEATURE:
<221> NAME/KEY: CDS
<222> LOCATION: (1)..(1200)
<223> OTHER INFORMATION: BP195

<400> SEQUENCE: 4 atg acc gaa acg ctg tac ccc gag ctg ccc acg act cgc agc tca ccg      48
Met Thr Glu Thr Leu Tyr Pro Glu Leu Pro Thr Thr Arg Ser Ser Pro
1               5                   10                  15 ctg gac ccg ccc gcg gaa ctg ggg gtg ttg cgc gag acc gaa ccc atc      96
Leu Asp Pro Pro Ala Glu Leu Gly Val Leu Arg Glu Thr Glu Pro Ile
            20                  25                  30 agc cgg ctg gcg ttc ccg gac ggc acc ctg ggg tgg ctg gtg acc agc     144
Ser Arg Leu Ala Phe Pro Asp Gly Thr Leu Gly Trp Leu Val Thr Ser
        35                  40                  45 cac gcg ctc gcg cgg gag gtg ctg gcc gac aac cgg ttc agc aac cgg     192
His Ala Leu Ala Arg Glu Val Leu Ala Asp Asn Arg Phe Ser Asn Arg
    50                  55                  60 gcc gag cta cag cac tcg ccg atc cgg gcg ggc ggc aaa ccc atc ccg     240
Ala Glu Leu Gln His Ser Pro Ile Arg Ala Gly Gly Lys Pro Ile Pro
65                  70                  75                  80 caa cag ccg ccg gcc aag ccc ggc atg ttc atc aac atg gac ggc cag     288
Gln Gln Pro Pro Ala Lys Pro Gly Met Phe Ile Asn Met Asp Gly Gln
                85                  90                  95 gag cac gcc aag tac cgg cgg ctg ctg acc ggc cag ttc acc gtc cgg     336
Glu His Ala Lys Tyr Arg Arg Leu Leu Thr Gly Gln Phe Thr Val Arg
            100                 105                 110 cgg atg aac cag ctc atc ccc cgg atc gag gcc atc gtg cgc gac cac     384
Arg Met Asn Gln Leu Ile Pro Arg Ile Glu Ala Ile Val Arg Asp His
        115                 120                 125 ctg gcc gac gtg cgg gca cag ggg ccg ggc gtc gac ctc gtg gag gcg     432
Leu Ala Asp Val Arg Ala Gln Gly Pro Gly Val Asp Leu Val Glu Ala
    130                 135                 140 ttc gcg ctg ccg gtg ccg tcg atg gtg atc tgc gag ctg ctg ggg gtg     480
Phe Ala Leu Pro Val Pro Ser Met Val Ile Cys Glu Leu Leu Gly Val
145                 150                 155                 160
```

| | | |
|---|---|---|
| tcc tac gag gag cgc gag tcg ttc cag cgg aac acg aag gcg ctg ttt<br>Ser Tyr Glu Glu Arg Glu Ser Phe Gln Arg Asn Thr Lys Ala Leu Phe<br>               165                    170                   175 | 528 |
| cac cct gac caa gga gtt tcg ccg aga tca ggg cgg cct tcg agc gga<br>His Pro Asp Gln Gly Val Ser Pro Arg Ser Gly Arg Pro Ser Ser Gly<br>180                    185                    190 | 576 |
| tcg agg act ttc gtc gcg gac ctc gtg cgg cgc aag cac gac gag ccg<br>Ser Arg Thr Phe Val Ala Asp Leu Val Arg Arg Lys His Asp Glu Pro<br>     195                    200                   205 | 624 |
| ggc gac gac atg ctc acg ggt ctg atc cag acc ggc gag ctg acc gac<br>Gly Asp Asp Met Leu Thr Gly Leu Ile Gln Thr Gly Glu Leu Thr Asp<br>210                    215                    220 | 672 |
| gag gaa gtc gcc aac atg ggg ctc ctc ctg ctc gtc gcc ggc cac gag<br>Glu Glu Val Ala Asn Met Gly Leu Leu Leu Leu Val Ala Gly His Glu<br>225                    230                    235                   240 | 720 |
| acg acc gcg aac atg ctc ggc atc ggc acg ctc acc ctg ctc ggc cac<br>Thr Thr Ala Asn Met Leu Gly Ile Gly Thr Leu Thr Leu Leu Gly His<br>                  245                    250                   255 | 768 |
| ccc gag cag ctg gcg gcg ctg aag gcc gac ccg tcc ttg atc gac aac<br>Pro Glu Gln Leu Ala Ala Leu Lys Ala Asp Pro Ser Leu Ile Asp Asn<br>                  260                    265                   270 | 816 |
| acg gtc gag gag ctg atg cgg tac ctg tcg atc gtc cag ttc ggc gcg<br>Thr Val Glu Glu Leu Met Arg Tyr Leu Ser Ile Val Gln Phe Gly Ala<br>     275                    280                   285 | 864 |
| tcc agg gtc gcc ctg gag gac gtg gaa ctg ggc ggg gtc acc gtc aag<br>Ser Arg Val Ala Leu Glu Asp Val Glu Leu Gly Gly Val Thr Val Lys<br>290                    295                    300 | 912 |
| gcg ggc gag ccg gtc agc atc tcg gtg atg gcc gcc aac cgc gac ccg<br>Ala Gly Glu Pro Val Ser Ile Ser Val Met Ala Ala Asn Arg Asp Pro<br>305                    310                    315                   320 | 960 |
| gcc aag ttc gac cgc ccg gag gag ttc gac atc cac cgg ccg gcg acc<br>Ala Lys Phe Asp Arg Pro Glu Glu Phe Asp Ile His Arg Pro Ala Thr<br>                  325                    330                   335 | 1008 |
| ggc cac gtg gcc ttc ggg cac ggc gtg cac cag tgc ctg ggc cag cag<br>Gly His Val Ala Phe Gly His Gly Val His Gln Cys Leu Gly Gln Gln<br>                    340                    345                   350 | 1056 |
| ttg gcg cgc atc gag atg cgc gtg ggg ttc aac gcc ctg ttc cgc gag<br>Leu Ala Arg Ile Glu Met Arg Val Gly Phe Asn Ala Leu Phe Arg Glu<br>     355                    360                   365 | 1104 |
| ttc ccg gac ctg cgg ctc gcg gtg ccg gcc tcg gag gtg ccg atg agg<br>Phe Pro Asp Leu Arg Leu Ala Val Pro Ala Ser Glu Val Pro Met Arg<br>370                    375                    380 | 1152 |
| gac gac atg gcc atc tac ggc gtg cac aag ctg ccg gtg acg ttc tca<br>Asp Asp Met Ala Ile Tyr Gly Val His Lys Leu Pro Val Thr Phe Ser<br>385                    390                    395                   400 | 1200 |
| tga | 1203 |

<210> SEQ ID NO 5
<211> LENGTH: 1404
<212> TYPE: DNA
<213> ORGANISM: Dactylosporangium variesporum IFO14104
<220> FEATURE:
<221> NAME/KEY: CDS
<222> LOCATION: (1)..(1401)
<223> OTHER INFORMATION: BP194

<400> SEQUENCE: 5

| | |
|---|---|
| atg aac tca gtc gca gaa att ttt gag aaa ata acc caa act gtc acc<br>Met Asn Ser Val Ala Glu Ile Phe Glu Lys Ile Thr Gln Thr Val Thr<br>1               5                   10                   15 | 48 |
| agc acc gct gca gac gta gca acc acg gtt acg gat aaa gtc aag tct | 96 |

```
Ser Thr Ala Ala Asp Val Ala Thr Thr Val Thr Asp Lys Val Lys Ser
             20                  25                  30 aat gag cag ttt caa acg ggc aag cag ttt ttg cat ggt caa gtg acc    144
Asn Glu Gln Phe Gln Thr Gly Lys Gln Phe Leu His Gly Gln Val Thr
             35                  40                  45 act agt acc agc ccc acc ggt tcc cgg gga ccc agc cag gac cgc ctg    192
Thr Ser Thr Ser Pro Thr Gly Ser Arg Gly Pro Ser Gln Asp Arg Leu
 50                  55                  60 gcc ctg cgg ctg ccg ccg gag tac acc gag cgc acc ccg ggt tgc ccg    240
Ala Leu Arg Leu Pro Pro Glu Tyr Thr Glu Arg Thr Pro Gly Cys Pro
 65                  70                  75                  80 ttc gac ccg tcg acc cgc ctg acc cgg atg ggc gct gag ggc ccc gtc    288
Phe Asp Pro Ser Thr Arg Leu Thr Arg Met Gly Ala Glu Gly Pro Val
             85                  90                  95 cac cag gtg acc atg ggc gac ggc gac acc gcc tgg ctg atc acg ggc    336
His Gln Val Thr Met Gly Asp Gly Asp Thr Ala Trp Leu Ile Thr Gly
            100                 105                 110 cac gag gag gcc cgc gcg gtg ccg gcg gac ccg agg ttc agc tcg gac    384
His Glu Glu Ala Arg Ala Val Pro Ala Asp Pro Arg Phe Ser Ser Asp
            115                 120                 125 cgc ttc cgc agc gaa cga gtc ctg cgc aaa ctc ccc gag acg ctg cgg    432
Arg Phe Arg Ser Glu Arg Val Leu Arg Lys Leu Pro Glu Thr Leu Arg
130                 135                 140 cag cgc atg acc gac ccg gcc gtc cgc gcg ggc aac ttc atc acc atg    480
Gln Arg Met Thr Asp Pro Ala Val Arg Ala Gly Asn Phe Ile Thr Met
145                 150                 155                 160 gac gcc ccg gag cac acc cgg tac cgc aag ctc ctg acc ggc cag ttc    528
Asp Ala Pro Glu His Thr Arg Tyr Arg Lys Leu Leu Thr Gly Gln Phe
            165                 170                 175 acc gtc cgc cgg atg cgc caa ctg acc ccg cgc atc cag gag atc gtc    576
Thr Val Arg Arg Met Arg Gln Leu Thr Pro Arg Ile Gln Glu Ile Val
            180                 185                 190 acc gag cac ctg gac gcc atg ctc gcg tcc ggc aac cgc gcc gac ctg    624
Thr Glu His Leu Asp Ala Met Leu Ala Ser Gly Asn Arg Ala Asp Leu
            195                 200                 205 gtg cag gcc ttc gcc ctc ccg gtg cct tct ctg gtg atc tgc gaa ctc    672
Val Gln Ala Phe Ala Leu Pro Val Pro Ser Leu Val Ile Cys Glu Leu
            210                 215                 220 ctc ggc gtc gcc tac gag gac cgg gcc cag ttc cag gaa cgg tcc ggc    720
Leu Gly Val Ala Tyr Glu Asp Arg Ala Gln Phe Gln Glu Arg Ser Gly
225                 230                 235                 240 acc ctc ctg cgc ctc aac gcc ccg gcc gag gac gtg gtg aag gcc gcg    768
Thr Leu Leu Arg Leu Asn Ala Pro Ala Glu Asp Val Val Lys Ala Ala
            245                 250                 255 gac gaa ctg cgc gcc ttc atg cgc ggc ctc atc cgg tcc aag cgc gcc    816
Asp Glu Leu Arg Ala Phe Met Arg Gly Leu Ile Arg Ser Lys Arg Ala
            260                 265                 270 gag ccc acc gac gac ctc ctg tcg ggc ttg atc gcc tcc gca ccg gac    864
Glu Pro Thr Asp Asp Leu Leu Ser Gly Leu Ile Ala Ser Ala Pro Asp
            275                 280                 285 ctg acc gac gac gag ctg gtg gtg atc tcc ctg ctg ctg ttg atc gcc    912
Leu Thr Asp Asp Glu Leu Val Val Ile Ser Leu Leu Leu Leu Ile Ala
            290                 295                 300 ggc cac gag acc acg gcg aac atg ctc gcc ctg ggc acg ttc gcg ttg    960
Gly His Glu Thr Thr Ala Asn Met Leu Ala Leu Gly Thr Phe Ala Leu
305                 310                 315                 320 ctg gaa cac ccg gag gag ctc gcc aaa ctc cgc gac gac ccg tcc ctc   1008
Leu Glu His Pro Glu Glu Leu Ala Lys Leu Arg Asp Asp Pro Ser Leu
            325                 330                 335 atc gac ggg gcg gtg gag gag ctg ctg cgc tac ctg tcg atc gtc cac   1056
```

-continued

```
                Ile Asp Gly Ala Val Glu Glu Leu Leu Arg Tyr Leu Ser Ile Val His
                            340                 345                 350 ctg ggg ccc gtg cgc acc acg ctg gag gag gtc gag atc gcc ggc gtc          1104
Leu Gly Pro Val Arg Thr Thr Leu Glu Glu Val Glu Ile Ala Gly Val
            355                 360                 365 cgc atc ccg gcc gac gaa acg gtg atc atc aac gtg ccg gtg gcc aac          1152
Arg Ile Pro Ala Asp Glu Thr Val Ile Ile Asn Val Pro Val Ala Asn
        370                 375                 380 cgc gac cca cgg gtc tac ggc gac cgg gac cag ctg gac gtg gcc cgc          1200
Arg Asp Pro Arg Val Tyr Gly Asp Arg Asp Gln Leu Asp Val Ala Arg
385                 390                 395                 400 ggc cgg gtg tcc cac ctg gcg ttc ggg cac ggc atc cac cag tgc ctg          1248
Gly Arg Val Ser His Leu Ala Phe Gly His Gly Ile His Gln Cys Leu
                405                 410                 415 ggg cag cag ttg gcg cgg gtg gag atg gcc gtc ggg ttc acc gag ctg          1296
Gly Gln Gln Leu Ala Arg Val Glu Met Ala Val Gly Phe Thr Glu Leu
            420                 425                 430 ctg cgc cgg ctg ccg ggc ttg cgc ctg gac ctg ccg gct tcg gag gtc          1344
Leu Arg Arg Leu Pro Gly Leu Arg Leu Asp Leu Pro Ala Ser Glu Val
        435                 440                 445 ccg ctg cgc agc gac atg ctg gtc tac ggc gtg cac agc ctc ccg gtc          1392
Pro Leu Arg Ser Asp Met Leu Val Tyr Gly Val His Ser Leu Pro Val
    450                 455                 460 gcc tgg gac tga                                                          1404
Ala Trp Asp
465

<210> SEQ ID NO 6
<211> LENGTH: 33
<212> TYPE: DNA
<213> ORGANISM: Artificial Sequence
<220> FEATURE:
<223> OTHER INFORMATION: Primer 1

<400> SEQUENCE: 6
catggatcct gaactgagtg aattgatatg caa                                     33

<210> SEQ ID NO 7
<211> LENGTH: 31
<212> TYPE: DNA
<213> ORGANISM: Artificial Sequence
<220> FEATURE:
<223> OTHER INFORMATION: Primer 2

<400> SEQUENCE: 7
cccaagcttc taccccatca acgcctgtac c                                       31

<210> SEQ ID NO 8
<211> LENGTH: 53
<212> TYPE: DNA
<213> ORGANISM: Artificial Sequence
<220> FEATURE:
<223> OTHER INFORMATION: Primer 3

<400> SEQUENCE: 8
gtaagatcta aataaggagg aataacatat ggcgctgacc accaccggca ccg               53

<210> SEQ ID NO 9
<211> LENGTH: 29
<212> TYPE: DNA
<213> ORGANISM: Artificial Sequence
<220> FEATURE:
<223> OTHER INFORMATION: Primer 4

<400> SEQUENCE: 9
```
tcaggatcct cggcacggag tgccgcgta                                    29

<210> SEQ ID NO 10
<211> LENGTH: 32
<212> TYPE: DNA
<213> ORGANISM: Artificial Sequence
<220> FEATURE:
<223> OTHER INFORMATION: Primer 5

<400> SEQUENCE: 10
taacatatga actcagtcgc agaaattttt ga                                32

<210> SEQ ID NO 11
<211> LENGTH: 32
<212> TYPE: DNA
<213> ORGANISM: Artificial Sequence
<220> FEATURE:
<223> OTHER INFORMATION: Primer 6

<400> SEQUENCE: 11
cgaactagtg gtcacttgac catgcaaaaa ct                                32

<210> SEQ ID NO 12
<211> LENGTH: 30
<212> TYPE: DNA
<213> ORGANISM: Artificial Sequence
<220> FEATURE:
<223> OTHER INFORMATION: Primer 7

<400> SEQUENCE: 12
ccgactagta ccgaaacgct gtaccccgag                                   30

<210> SEQ ID NO 13
<211> LENGTH: 30
<212> TYPE: DNA
<213> ORGANISM: Artificial Sequence
<220> FEATURE:
<223> OTHER INFORMATION: Primer 8

<400> SEQUENCE: 13
cctggatcct catgagaacg tcaccggcag                                   30

<210> SEQ ID NO 14
<211> LENGTH: 29
<212> TYPE: DNA
<213> ORGANISM: Artificial Sequence
<220> FEATURE:
<223> OTHER INFORMATION: Primer 9

<400> SEQUENCE: 14
ggccatatga ccgaaacgct gtaccccga                                    29

<210> SEQ ID NO 15
<211> LENGTH: 28
<212> TYPE: DNA
<213> ORGANISM: Artificial Sequence
<220> FEATURE:
<223> OTHER INFORMATION: Primer 10

<400> SEQUENCE: 15
gcgactagta ccagccccac cggttccc                                     28

<210> SEQ ID NO 16
<211> LENGTH: 30
<212> TYPE: DNA
<213> ORGANISM: Artificial Sequence

```
<220> FEATURE:
<223> OTHER INFORMATION: Primer 11

<400> SEQUENCE: 16
ccgggatcct cagtcccagg cgaccgggag                                30

<210> SEQ ID NO 17
<211> LENGTH: 26
<212> TYPE: DNA
<213> ORGANISM: Artificial Sequence
<220> FEATURE:
<223> OTHER INFORMATION: Primer 12

<400> SEQUENCE: 17
gcgcatatga ccagccccac cggttc                                   26

<210> SEQ ID NO 18
<211> LENGTH: 31
<212> TYPE: DNA
<213> ORGANISM: Artificial Sequence
<220> FEATURE:
<223> OTHER INFORMATION: Primer 13

<400> SEQUENCE: 18
accactagtg cgctgaccac caccggcacc g                             31

<210> SEQ ID NO 19
<211> LENGTH: 31
<212> TYPE: DNA
<213> ORGANISM: Artificial Sequence
<220> FEATURE:
<223> OTHER INFORMATION: Primer 14

<400> SEQUENCE: 19
gggagatctt caggcgctgc gcggcccat c                              31

<210> SEQ ID NO 20
<211> LENGTH: 31
<212> TYPE: DNA
<213> ORGANISM: Artificial Sequence
<220> FEATURE:
<223> OTHER INFORMATION: Primer 15

<400> SEQUENCE: 20
acccatatgg cgctgaccac caccggcacc g                             31

<210> SEQ ID NO 21
<211> LENGTH: 30
<212> TYPE: DNA
<213> ORGANISM: Artificial Sequence
<220> FEATURE:
<223> OTHER INFORMATION: Primer 16

<400> SEQUENCE: 21 gcccccata tggcgctgac caccaccggc                                30

<210> SEQ ID NO 22
<211> LENGTH: 30
<212> TYPE: DNA
<213> ORGANISM: Artificial Sequence
<220> FEATURE:
<223> OTHER INFORMATION: Primer 17

<400> SEQUENCE: 22
gccactagtt caggcgctgc gcggcccat                                30
```

```
<210> SEQ ID NO 23
<211> LENGTH: 27
<212> TYPE: DNA
<213> ORGANISM: Artificial Sequence
<220> FEATURE:
<223> OTHER INFORMATION: Primer 18

<400> SEQUENCE: 23
cggactagtc tactcgatca ccttgat                                          27

<210> SEQ ID NO 24
<211> LENGTH: 32
<212> TYPE: DNA
<213> ORGANISM: Artificial Sequence
<220> FEATURE:
<223> OTHER INFORMATION: Primer 19

<400> SEQUENCE: 24
cgcactagtc agtcccaggc gaccgggagg ct                                    32
```